United States Patent
Day et al.

(10) Patent No.: US 8,227,428 B2
(45) Date of Patent: Jul. 24, 2012

(54) ANTI-INFAMMATORY MACROLIDE

(75) Inventors: Caroline Jane Day, Stevenage (GB);
Julien Bruno Douillet, Stevenage (GB);
Darko Filic, Zagreb (HR); Leanda Jane Kindon, Stevenage (GB); Goran Kragol, Zagreb (HR); Zorica Marusic-Istuk, Zagreb (HR)

(73) Assignee: Glaxo Group Limited, Greenford, Middlesex (GB)

( * ) Notice: Subject to any disclaimer, the term of this patent is extended or adjusted under 35 U.S.C. 154(b) by 210 days.

(21) Appl. No.: 12/695,272

(22) Filed: Jan. 28, 2010

(65) Prior Publication Data

US 2010/0197623 A1    Aug. 5, 2010

Related U.S. Application Data

(60) Provisional application No. 61/148,609, filed on Jan. 30, 2009.

(51) Int. Cl.
*A61K 31/70* (2006.01)
*C07H 17/08* (2006.01)

(52) U.S. Cl. ......................... 514/29; 536/7.4
(58) Field of Classification Search .................. 536/7.4
See application file for complete search history.

(56) References Cited

U.S. PATENT DOCUMENTS

| | | | |
|---|---|---|---|
| 5,250,518 | A | 10/1993 | Kobrehel et al. |
| 6,110,965 | A | 8/2000 | Lazarevski et al. |
| 7,910,559 | B2 | 3/2011 | Culic et al. |
| 8,080,529 | B2 | 12/2011 | Alihodzic et al. |
| 2008/0221046 | A1 * | 9/2008 | Culic et al. ............ 514/29 |
| 2008/0241959 | A1 | 10/2008 | Culic et al. |
| 2010/0197623 | A1 | 8/2010 | Day et al. |

FOREIGN PATENT DOCUMENTS

| | | |
|---|---|---|
| EP | 0126344 A2 | 11/1984 |
| EP | 0895999 A1 | 2/1999 |
| WO | 99/51616 A1 | 10/1999 |
| WO | 02/087596 A2 | 11/2002 |
| WO | 2004/005310 A2 | 1/2004 |
| WO | 2004/101586 A1 | 11/2004 |
| WO | 2006/77501 A2 | 7/2006 |
| WO | 2006/87644 A2 | 8/2006 |
| WO | 2006/106440 A1 | 10/2006 |
| WO | 2010/086349 A1 | 8/2010 |

OTHER PUBLICATIONS

Culic, et al., "Anti-inflammatory effects of macrolide antibiotics" 2001; European Journal of Pharmacology; vol. 429 (1-3); pp. 209-229.

Labro,"Anti-inflammatory activity of macrolides: a new therapeutic potential?" 1998; Journal of Antimicrobial Chemotherapy; vol. 41, Suppl. B; pp. 37-46.

Mikasa, et al., "The anti-inflammatory effect of erythromycin in zymosan-induced peritonitis of mice" 1992; Journal of Antimircrobial Chemotherapy; vol. 30 (3); pp. 339-348.

Koyama, et al., "Erythromycin and diffuse panbronchiolitis", Thorax, 1997; vol. 52; pp. 915-918.

Miyatake, et al.,"Erythromycin reduces the severity of bronchial hyperresponsiveness in asthma" 1991; Chest; vol. 99; pp. 670-673.

Abdelghaffar, et al., "Erythromycin A-derived macrolides modify the functional activities of human neutrophils by altering the phospholipase D-phosphatidate phosphohydrolase transduction pathway: L-cladinose is involved both in alterations of neutrophil functions and modulation of this transductional pathway." 1997; Journal of Immunology; vol. 159; pp. 3995-4005.

Jaffe, et al., "Long-Term azithromycin may improve lung function in children with cystic fibrosis." Lancet, 1998; vol. 351; p. 420.

Tamaoki, et al., "Macrolide antibiotics protect against endotoxin-induced vascular leakage and neutrophil accumulation in rat trachea." 1994; Antimicrobial Agents and Chemotherapy; vol. 38(7); pp. 1641-1643.

Labro, "Immunomodulatory Actions of Antibacterial Agents" 1996; Clinical Immunotherapeutics; vol. 6; pp. 454-464.

* cited by examiner

*Primary Examiner* — Elli Peselev
(74) *Attorney, Agent, or Firm* — Karen L. Prus

(57) ABSTRACT

The compound 3'-N-demethyl-4"-O-(2-diethylaminoethanoyl)-6-O-methyl-9a-aza-9a-homoerythromycin A, having the Formula (I):

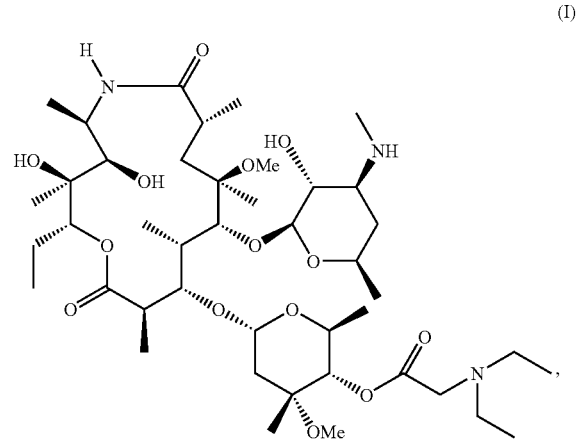

(I)

or a salt thereof, compositions comprising the compound, its use in the treatment of neutrophil dominated inflammatory diseases, and methods for its preparation.

11 Claims, 7 Drawing Sheets

*no plasma sample taken at 15 min

Figure 2: Mass spectrum of decomposition peak A and derived molecular structure

Figure 3: XRPD pattern of amorphous form
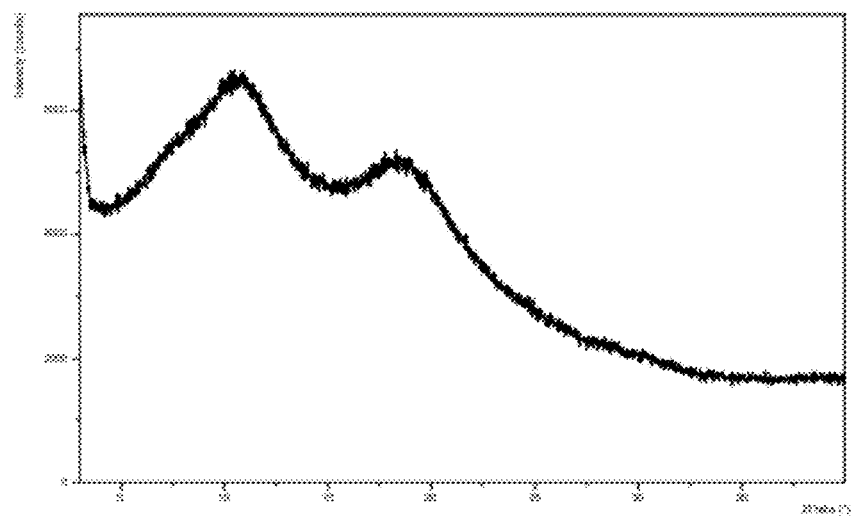
Figure 4: XRPD pattern of Form 1
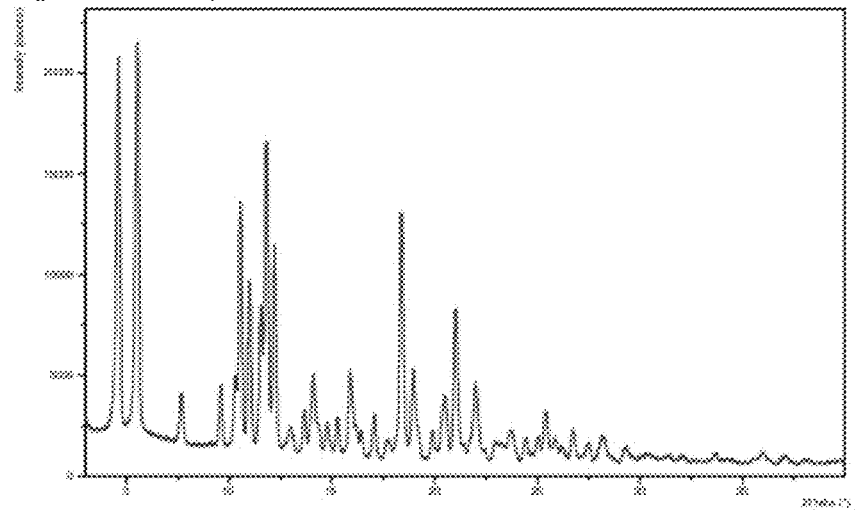
Figure 5: DSC of Form 1
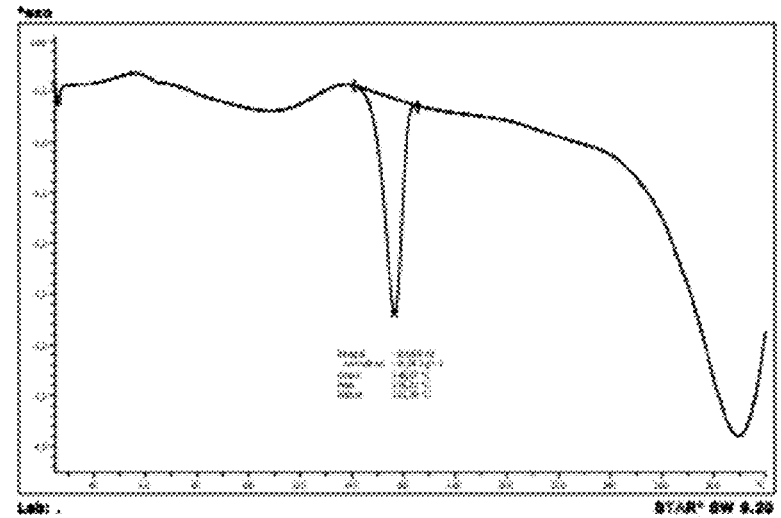

Figure 6: TGA of Form 1
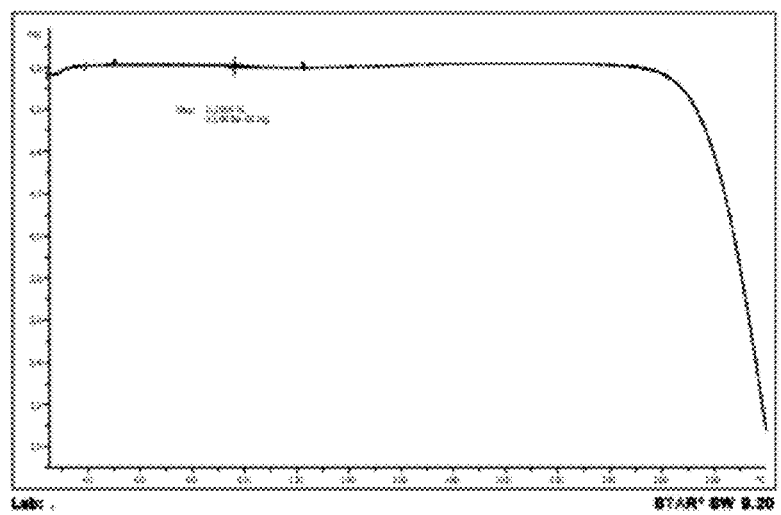
Figure 7: XRPD pattern of Form 2
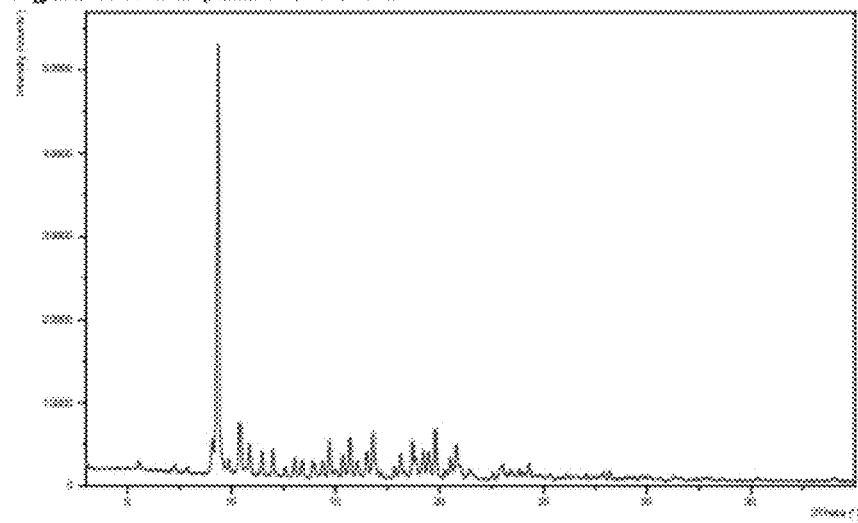
Figure 8: DSC of Form 2
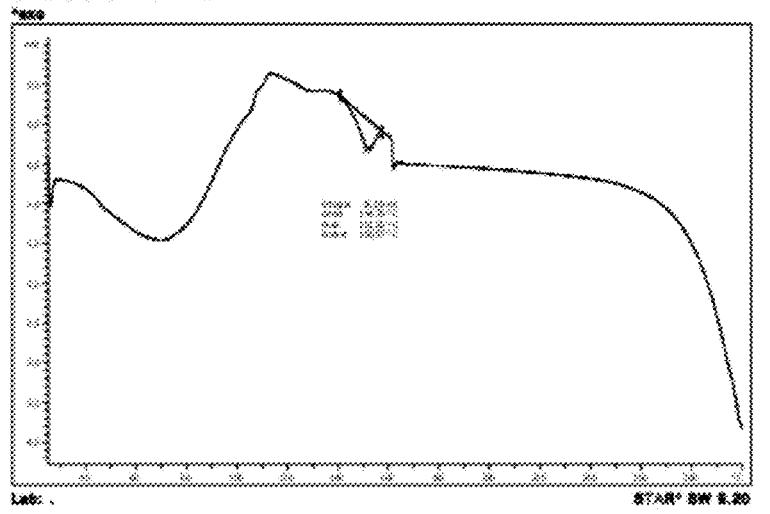

Figure 9: TGA of Form 2
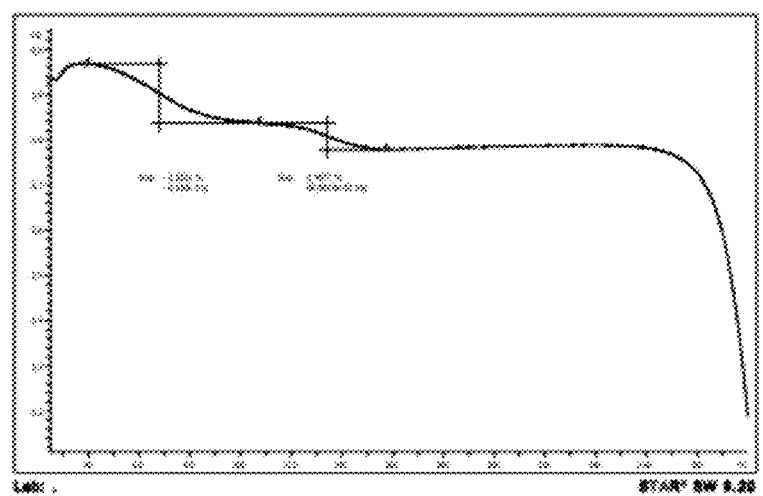
Figure 10: XRPD pattern of Form 3
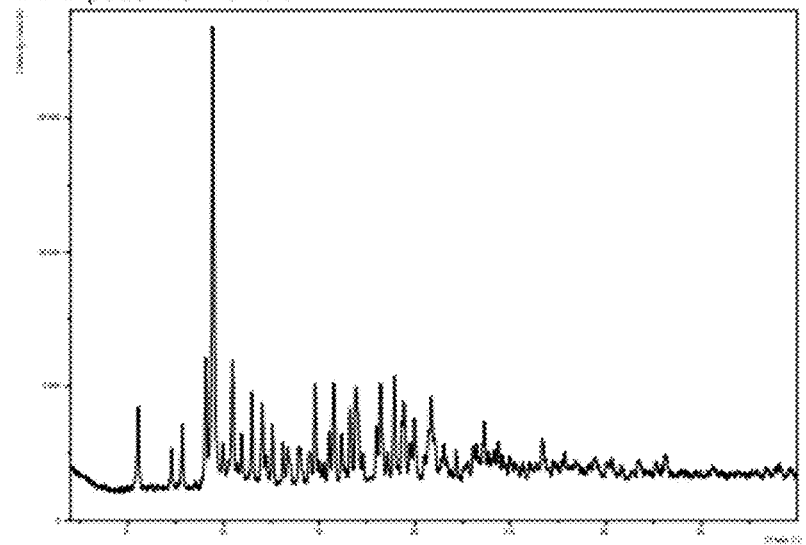
Figure 11: Raman spectrum of Form 3
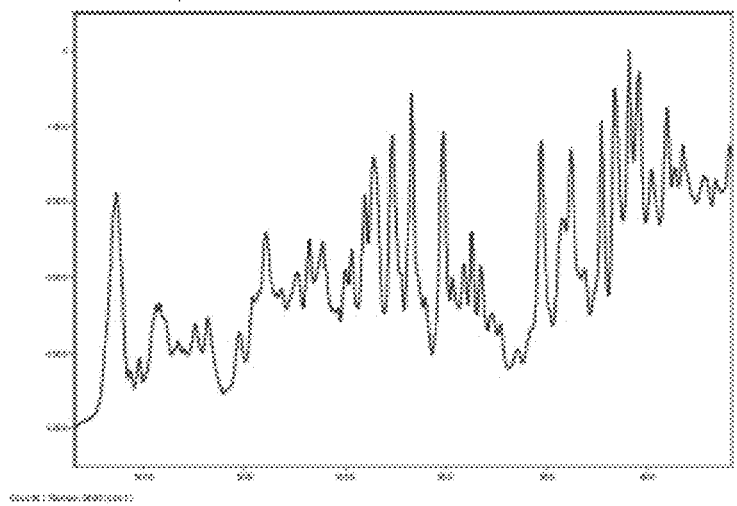

Figure 12: Raman spectrum of Form 4
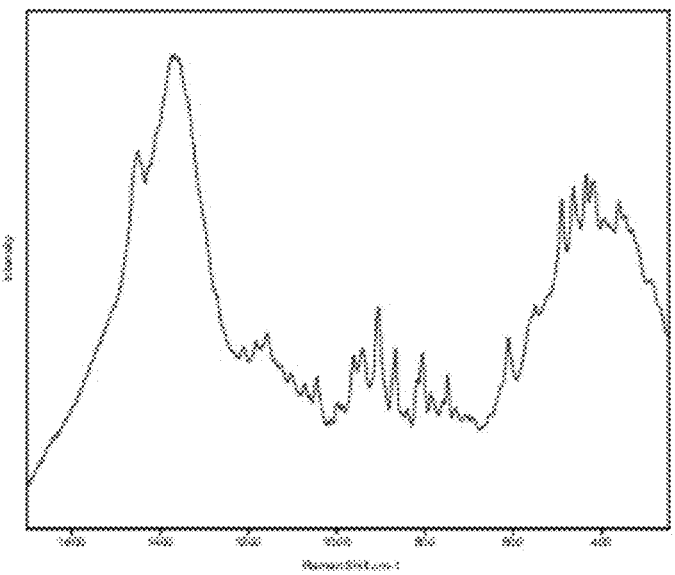
Figure 13: Raman spectrum of Form 5
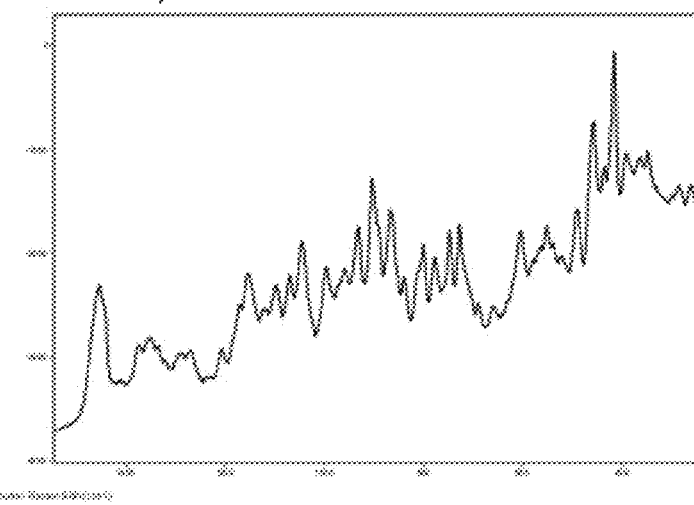
Figure 14: Raman spectrum of Form 6
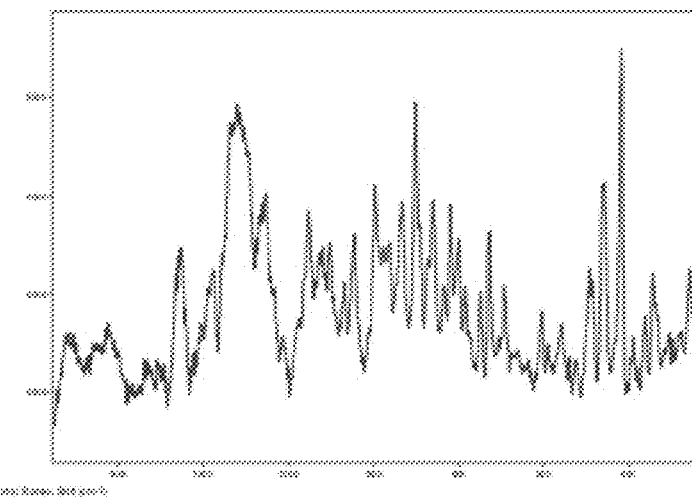

Figure 15: Raman spectrum of Form 7
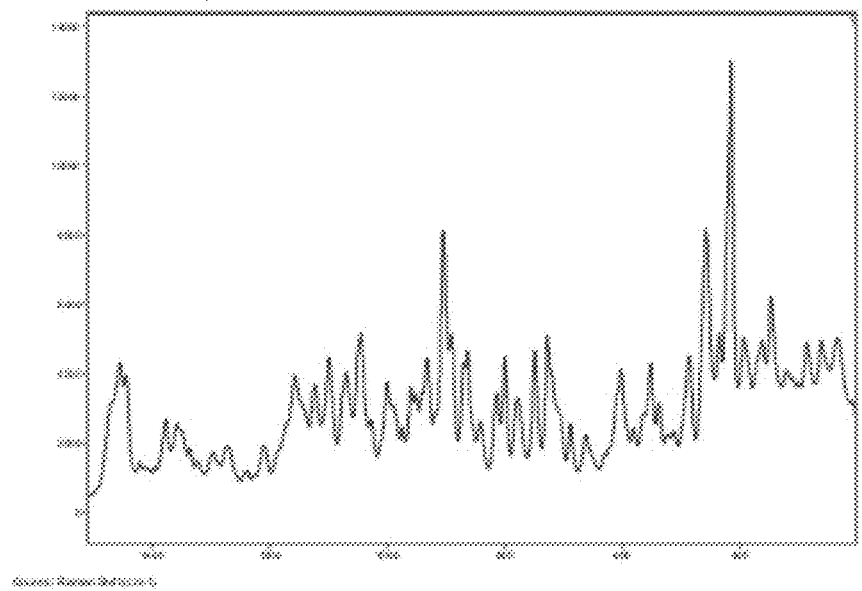
Figure 16: Raman spectrum of Form 8
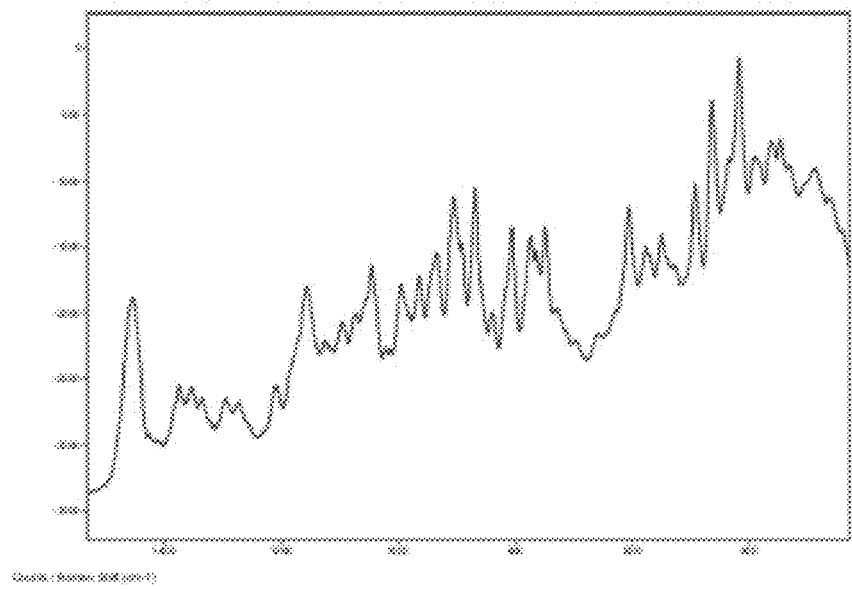

ANTI-INFAMMATORY MACROLIDE

This application is filed pursuant to 35 U.S.C. §111(a) as a United States Application which claims priority from U.S. Provisional No. 61/148,609 filed in the United States on Jan. 30, 2009 the contents of which are incorporated herein by reference.

TECHNICAL FIELD

The present invention relates to a 4"-O-substituted 6-O-methyl 9a lactam macrolide molecule useful in the treatment of inflammatory diseases. More particularly, the invention relates to 3'-N-demethyl-4"-O-(2-diethylaminoethanoyl)-6-O-methyl-9a-aza-9a-homoerythromycin A, useful in the treatment of neutrophil dominated inflammatory diseases, especially in the treatment of neutrophil dominated inflammatory diseases resulting from neutrophilic infiltration and/or diseases associated with altered cellular functionality of neutrophils, to the intermediates for its preparation, to methods for its preparation, to its use as a therapeutic agent, and to salts thereof.

BACKGROUND

Inflammation is the final common pathway of various insults, such as infection, trauma, and allergies to the human body. It is characterized by activation of the immune system with recruitment and activation of inflammatory cells and production of pro-inflammatory mediators.

Most inflammatory diseases are characterized by enhanced accumulation of differing proportions of inflammatory cells, including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage.

One form of inflammatory response is neutrophilic inflammation which is characterized by infiltration of the inflamed tissue by neutrophilic polymorphonuclear leukocytes (PMN, i.e. neutrophils), which are a major component of host defence. Neutrophils are activated by a great variety of stimuli and are involved in a number of clinical conditions and diseases where they play a pivotal role. Such diseases may be classified according to the major neutrophil-activating event (Table 3, page 638 of V. Witko-Sarsat et al., *Laboratory Investigation* (2000) 80(5), 617-653). Tissue infection by extracellular bacteria represents the prototype of this inflammatory response. On the other hand, various non-infectious diseases are characterized by extravascular recruitment of neutrophils. These non-infectious inflammatory diseases may be the result of an intermittent resurgence (e.g. flare in autoimmune diseases such as rheumatoid arthritis), or continuous generation (e.g. chronic obstructive pulmonary disease (COPD)) of inflammatory signals arising from underlying immune dysfunction. Non-infectious inflammatory disease include COPD, cystic fibrosis (CF), diffuse panbronchiolitis (DPB), bronchiolitis obliterans (BOS), bronchitis, bronchiectasis, emphysema, acute respiratory distress syndrome (ARDS, known also as adult respiratory distress syndrome or respiratory distress syndrome, RDS), as well as glomerulonephritis, rheumatoid arthritis, gouty arthritis, ulcerative colitis, certain dermatoses such as psoriasis and vasculitis. In these conditions neutrophils are thought to play a crucial role in the development of tissue injury which, when persistent, can lead to the irreversible destruction of the normal tissue architecture with consequent organ dysfunction. Consequently, correlation between neutrophil number in sputum or bronchoalveolar lavage fluid and disease severity and decline in lung function is demonstrated in patients with chronic obstructive pulmonary disease (Di Stefano et al., *Am J Respir Crit. Care Med.* (1998), 158(4): 1277-1285), cystic fibrosis (Sage) SD et al., *J Pediatr.* (2002), 141(6): 811-817), diffuse panbronchiolitis (Yanagihara K et al., *Int J Antimicrob Agents*. (2001), 18 Suppl 1: S83-87), bronchiolitis obliterans (Devouassoux G et al., *Transpl Immunol*. (2002), 10(4): 303-310), bronchitis (Thompson A B et al., *Am Rev Respir Dis*. (1989), 140(6): 1527-1537), bronchiectasis (Sepper R et al., *Chest* (1995), 107(6): 1641-1647), acute respiratory distress syndrome (Weiland J E et al., *Am Rev Respir Dis*. (1986), 133(2): 218-225), to name a few. In addition, there is increasing evidence of neutrophil inflammation in asthmatics, particularly in patients with severe disease and patients who smoke (Jatakanon A et al., *Am J Respir Crit. Care Med*. (1999), 160: 1532-1539; Chalmers G W et al., *Chest* (2001), 120: 1917-1922). Evidence of the importance of neutrophils in several lung diseases has prompted a search for drugs that inhibit neutrophilic infiltration into lungs and consequent inflammation (reviewed in Barnes P J, *J Allergy Clin Immunol*. (2007), 119(5): 1055-1062).

It is known that many antibiotics, in particular the class of erythromycin-based macrolides, have anti-inflammatory properties in addition to their antibacterial activity (*Clin. Immunother*. (1996) 6, 454-464), *J. Antimicrob. Chemother*. (1998) 41, Suppl. B 37-46). In the international patent application publication WO02/087596 (Pliva) the anti-inflammatory activity of azithromycin, a 15-membered azalide antibacterial agent, has been described. Thus, the interest of the scientific community has turned towards the anti-inflammatory and immunomodulatory properties of erythromycin and derivatives thereof (*J. Antimicrob. Chemother*. (1998), 41, Suppl. B, 37-46). This activity is well documented both in clinical studies and in in vivo and in vitro experiments. For example, macrolides have been found to be effective in the treatment of inflammatory diseases such as panbronchiolitis (*Thorax* (1997), 52, 915-918), bronchial asthma (*Chest*, (1991), 99, 670-673) and cystic fibrosis (*The Lancet* (1998) 351, 420), both in animal models of inflammation, for instance zymosan-induced peritonitis in mice (*J. Antimicrob. Chemother*. (1992) 30, 339-348) and endotoxin-induced accumulation of neutrophils in rat trachea (*Antimicrobial Agents and Chemotherapy* (1994) 38, 1641-1643], and in in vitro studies on immune system cells, such as neutrophils (*J. Immunology* (1997) 159, 3395-4005).

The particular therapeutic efficacy of macrolide compounds in diseases where conventional anti-inflammatory drugs, for instance corticosteroids, have been found to be ineffective (*Thorax* (1997) 52, 915-918, already cited) justifies the great interest in this new potential class of anti-inflammatories. However, the strong antibacterial activity that conventional macrolide compounds have does not allow their broader use in the chronic treatment of inflammatory processes not caused by pathogenic microorganisms, since this could give rise to the rapid development of resistant strains.

Based on the foregoing, there exists a significant need to identify compounds having a biological profile which demonstrates the ability to inhibit neutrophil dominated inflammation whilst not having anti-bacterial activity. Such compounds should also have a stability which renders them suitable for development as a therapeutic treatment.

WO06/87644 discloses macrolide compounds represented by Formula (I) below:

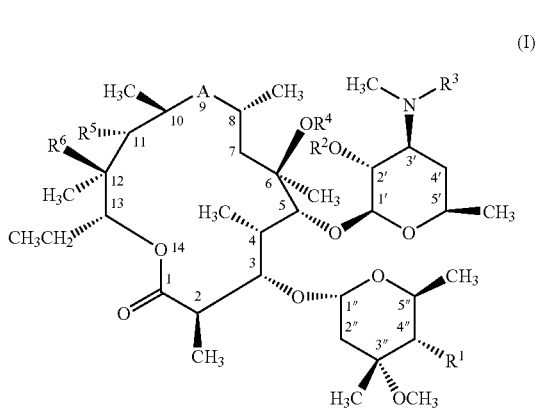

(I)

wherein
A is a bivalent radical selected from —C(O)—, —NHC(O)—, —C(O)NH—, —N($R^7$)$CH_2$—, —$CH_2$N($R^7$)—, —CH(OH)— and —C(=NO$R^7$)—;

$R^1$ is —OC(O)($CH_2$)$_n$N$R^8R^9$, —O—($CH_2$)$_n$N$R^8R^9$, —OC(O)N($R^7$)($CH_2$)$_n$N$R^8R^9$,

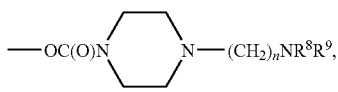

—O($CH_2$)$_n$CN, —OC(O)($CH_2$)$_n$N($CH_2$)$_n$N$R^8R^9$, or —OC(O)CH=$CH_2$ with the proviso that if $R^1$ is —OC(O)CH=$CH_2$, $R^3$ cannot be methyl;

$R^2$ is hydrogen or a hydroxyl protecting group;

$R^3$ is hydrogen, unsubstituted $C_{1-4}$ alkyl or $C_{1-4}$ alkyl substituted at terminal carbon atom with CN or $NH_2$ group, or $C_{1-5}$ alkanoyl;

$R^4$ is hydrogen, $C_{1-4}$ alkyl or $C_{2-6}$ alkenyl or a hydroxyl protecting group 1;

$R^5$ is hydroxy, methoxy group, —OC(O)($CH_2$)$_n$N$R^8R^9$—O—($CH_2$)$_n$N$R^8R^9$ or —O($CH_2$)$_n$CN;

$R^6$ is hydroxy; or $R^5$ and $R^6$ taken together with the intervening atoms form a cyclic group having the following structure:

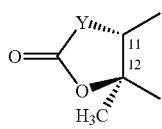

wherein Y is a bivalent radical selected from —$CH_2$—, —CH(CN)—, —O—, —N($R^7$)— and —CH(S$R^7$)—;

$R^7$ is hydrogen or $C_{1-6}$alkyl;

$R^8$ and $R^9$ are each independently hydrogen, $C_{3-7}$ cycloalkyl, $C_{1-18}$ alkyl, wherein $C_{1-18}$ alkyl is:
(i) uninterrupted or interrupted by 1-3 bivalent radical groups selected from —O—, —S— and —N($R^7$)—; and/or
(ii) unsubstituted or substituted by 1-3 groups selected from halogen, OH, $NH_2$, N—($C_1$-$C_6$)alkylamino (preferably N-methylamino or N-ethylamino), N,N-di($C_1$-$C_6$-alkyl) amino (preferably dimethylamino, diethylamino or di-isopropylamino), CN, $NO_2$, $OCH_3$, a $C_{3-8}$ membered non-aromatic ring which is saturated or unsaturated a non-aromatic heterocyclic ring containing 2-6 carbon atoms which is saturated or unsaturated containing from 1-2 heteroatoms selected from oxygen, sulphur and nitrogen, alkylcarbonylalkoxy and alkoxycarbonylamino; or $R^8$ and $R^9$ taken together with nitrogen to which they are attached form a non-aromatic heterocyclic ring containing 2-6 carbon atoms which is:
i) saturated or unsaturated containing from 0 or 1 additional heteroatoms selected from oxygen, sulphur and nitrogen; and/or
ii) unsubstituted or substituted by 1-2 groups selected from $C_{1-3}$alkanoyl and $C_{1-6}$alkyl, wherein $C_{1-6}$alkyl is uninterrupted or is interrupted by 1-3 bivalent radical groups selected from —O—, —S— and —N($R^7$)—, and/or being unsubstituted or substituted by 1-2 groups selected from OH, $NH_2$, a non-aromatic heterocyclic ring containing 2-6 carbon atoms which is unsubstituted or is substituted by group selected from $C_{1-4}$ alkyl, halo, $NH_2$, OH, SH, $C_{1-6}$ alkoxy and $C_{1-4}$ hydroxyalkyl, a $C_{3-7}$ cycloalkyl which is unsubstituted or is substituted by group selected from $C_{1-4}$ alkyl, halo, $NH_2$, OH, SH, $C_{1-6}$alkoxy and $C_{1-4}$ hydroxyalkyl;

n is an integer from 1 to 8;

and pharmaceutically acceptable derivatives thereof. It describes these compounds as having anti-inflammatory activity.

SUMMARY OF THE INVENTION

It has now been found that the compound according to the present invention, generically disclosed in WO06/87644, and having a specific substitution pattern, exhibits an improved profile over those compounds specifically disclosed in WO06/87644.

The present invention relates to 3'-N-demethyl-4"-O-(2-diethylaminoethanoyl)-6-O-methyl-9a-aza-9a-homoerythromycin A, a compound having the Formula (I):

(I)

or a salt thereof.

The present invention also relates to pharmaceutical compositions comprising the compound of Formula (I) or a pharmaceutically acceptable salt thereof.

Furthermore, the present invention also relates to methods of treating neutrophil dominated inflammatory diseases resulting from neutrophilic infiltration and/or diseases associated with altered cellular functionality of neutrophils comprising administration of a therapeutically effective amount of the compound of Formula (I) or a pharmaceutically acceptable salt thereof to a subject in need thereof.

According to another aspect, the invention relates to the compound of Formula (I) or a pharmaceutically acceptable salt thereof for use in human or veterinary medical therapy.

In another aspect, the invention relates to the compound of Formula (I) or a pharmaceutically acceptable salt thereof, for use in the treatment of neutrophil dominated inflammatory diseases resulting from neutrophilic infiltration and/or diseases associated with altered cellular functionality of neutrophils.

In another aspect, the invention relates to the use of the compound of Formula (I) or a pharmaceutically acceptable salt thereof in the manufacture of a medicament for the treatment of neutrophil dominated inflammatory diseases resulting from neutrophilic infiltration and/or diseases associated with altered cellular functionality of neutrophils.

BRIEF DESCRIPTION OF THE DRAWINGS

FIG. 2: shows the structure of the major degradant of comparative Example 2 derived from its mass spectrum.

FIG. 3: shows XRPD pattern of amorphous form of 3'-N-demethyl-4"-O-(2-diethylaminoethanoyl)-6-O-methyl-9a-aza-9a-homoerythromycin A.

FIG. 4: XRPD pattern of Form 1 of 3'-N-demethyl-4"-O-(2-diethylaminoethanoyl)-6-O-methyl-9a-aza-9a-homoerythromycin A.

FIG. 5: DSC of Form 1 of 3'-N-demethyl-4"-O-(2-diethylaminoethanoyl)-6-O-methyl-9a-aza-9a-homoerythromycin A.

FIG. 6: TGA of Form 1 of 3'-N-demethyl-4"-O-(2-diethylaminoethanoyl)-6-O-methyl-9a-aza-9a-homoerythromycin A.

FIG. 7: XRPD pattern of Form 2 of 3'-N-demethyl-4"-O-(2-diethylaminoethanoyl)-6-O-methyl-9a-aza-9a-homoerythromycin A.

FIG. 8: DSC of Form 2 of 3'-N-demethyl-4"-O-(2-diethylaminoethanoyl)-6-O-methyl-9a-aza-9a-homoerythromycin A.

FIG. 9: TGA of Form 2 of 3'-N-demethyl-4"-O-(2-diethylaminoethanoyl)-6-O-methyl-9a-aza-9a-homoerythromycin A.

FIG. 10: XRPD pattern of Form 3 of 3'-N-demethyl-4"-O-(2-diethylaminoethanoyl)-6-O-methyl-9a-aza-9a-homoerythromycin A.

FIG. 11: Raman spectrum of Form 3 of 3'-N-demethyl-4"-O-(2-diethylaminoethanoyl)-6-O-methyl-9a-aza-9a-homoerythromycin A.

FIG. 12: Raman spectrum of Form 4 of 3'-N-demethyl-4"-O-(2-diethylaminoethanoyl)-6-O-methyl-9a-aza-9a-homoerythromycin A.

FIG. 13: Raman spectrum of Form 5 of 3'-N-demethyl-4"-O-(2-diethylaminoethanoyl)-6-O-methyl-9a-aza-9a-homoerythromycin A.

FIG. 14: Raman spectrum of Form 6 of 3'-N-demethyl-4"-O-(2-diethylaminoethanoyl)-6-O-methyl-9a-aza-9a-homoerythromycin A.

FIG. 15: Raman spectrum of Form 7 of 3'-N-demethyl-4"-O-(2-diethylaminoethanoyl)-6-O-methyl-9a-aza-9a-homoerythromycin A.

FIG. 16: Raman spectrum of Form 8 of 3'-N-demethyl-4"-O-(2-diethylaminoethanoyl)-6-O-methyl-9a-aza-9a-homoerythromycin A.

DESCRIPTION OF THE EMBODIMENTS

Figure 1A:
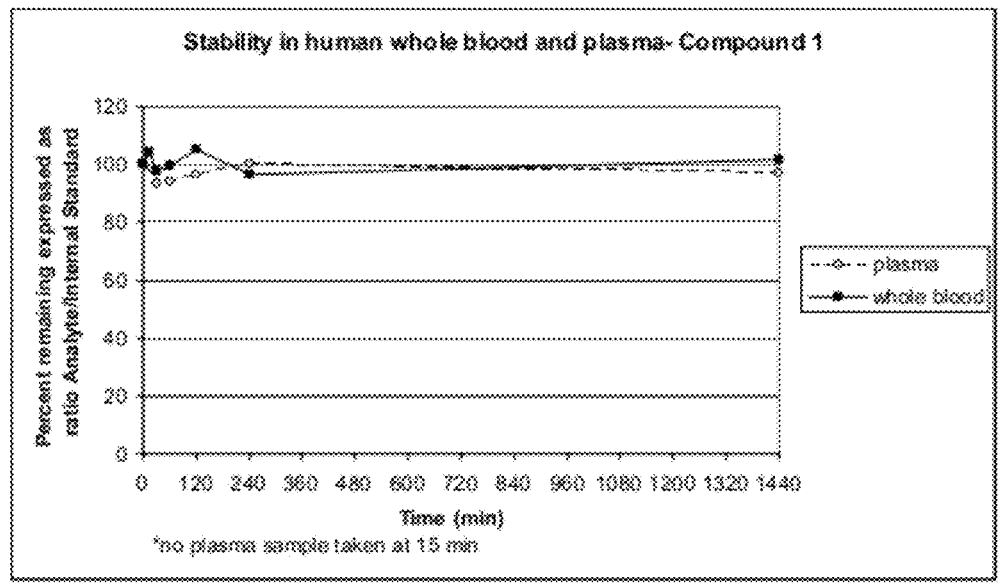
FIGS. 1A to 1C: show stability in human whole blood and plasma for Examples 1, 2 and 3, respectively within 24 hours.

It will be understood that the present invention covers all combinations of aspects, suitable, convenient and preferred groups described herein.

References hereinafter to "a compound according to the invention" or "compounds of the present invention" include both the compound of Formula (I) (whether in solvated or unsolvated form), its salts or its pharmaceutically acceptable salts (whether in solvated or unsolvated form).

Throughout the specification and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "inert solvent" or "solvent inert to the reaction", as used herein, refers to a solvent that cannot react with the dissolved compounds including non-polar solvent such as hexane, toluene, diethyl ether, diisopropylether, chloroform, ethyl acetate, THF, dichloromethane; polar aprotic solvents such as acetonitrile, acetone, N,N-dimethylformamide, N,N-dimethylacetamide, dimethyl sulfoxide, pyridine, and polar protic solvents such as lower alcohol, acetic acid, formic acid and water.

The term "lower alcohol", as used herein, refers to a $C_{1-4}$ alcohol, such as for example, methanol, ethanol, propanol, isopropanol, butanol, t-butanol, and the like.

In one aspect the present invention provides the compound of Formula (I) or a salt thereof wherein the salt is a pharmaceutically acceptable salt. For a review on suitable salts see Berge et al., J. Pharm. Sci., 66 (1977) 1-19. Suitable pharmaceutically acceptable salts can include acid addition salts.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate (eg L-tartrate), citrate, formate, gluconate, succinate, salicylate, propionate, pyruvate, hexanoate, oxalate, oxaloacetate, trifluoroacetate, saccharate, glutamate, aspartate, benzoate, alkyl or aryl sulphonates (eg methanesulphonate, ethanesulphonate, benzenesulphonate or p-toluenesulphonate) and isethionate. In one aspect, the compound of Formula (I) may be in the form of hydrochloride or acetate salt. In a further aspect, the compound of Formula (I) may be in the form of succinate, benzoate, L-tartrate, hydrochloride (specifically dihydrochloride) or phosphate salt.

Those skilled in the art of chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of the compound of Formula (I) may form solvates (e.g. hydrates) and the invention also includes all such solvates.

In one aspect, the compound of Formula (I) may be in the form of a pharmaceutically acceptable salt, solvate or solvate of salt. In a further aspect, the compound of Formula (I) of the present invention may be in the form of a pharmaceutically acceptable salt.

With regard to stereoisomers, the compound of Formula (I) has more than one asymmetric carbon atom. In Formula (I) as drawn, the solid wedge shaped bond indicates that the bond is above the plane of the paper. The broken bond indicates that the bond is below the plane of the paper.

The compound of Formula (I) may be in crystalline or amorphous form. Furthermore, some of the crystalline forms of the compound of Formula (I) may exist as polymorphs, which are also included in the present invention.

In one particular embodiment, the present invention relates to 3'-N-demethyl-4"-O-(2-diethylaminoethanoyl)-6-O-methyl-9a-aza-9a-homoerythromycin A, a compound having the Formula (I):

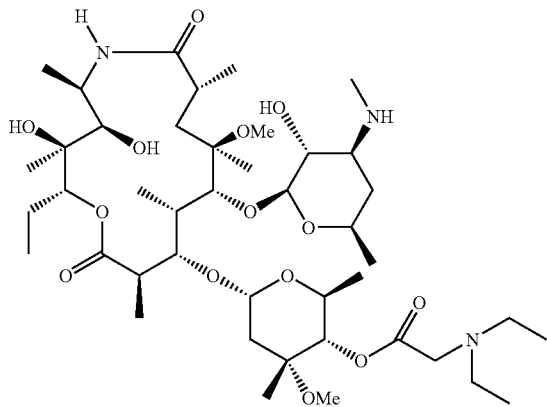

(I)

or a salt thereof.

In one aspect of the invention, a compound having the Formula (I) is Form 1, characterized by the XRPD pattern expressed in terms of 2 theta angles according to the procedures described herein and shown in FIG. 4. In a further aspect the XRPD pattern expressed in terms of 2 theta angles according to the procedures described herein comprises 2 theta angles (2Θ/°) in at least five positions selected from the group consisting of: 4.6, 5.6, 7.7, 9.6, 10.6, 11.0, 11.6, 11.8, 12.2, 14.1, 15.9, 18.4, 19.0, 20.5, 21.1 and 22.0 degrees, which correspond respectively to d-spacings at 19.1, 15.9, 11.5, 9.2, 8.4, 8.0, 7.7, 7.5, 7.2, 6.3, 5.6, 4.8, 4.7, 4.3, 4.2 and 4.0 Angstroms (Å). In a yet further aspect of the invention the XRPD pattern expressed in terms of 2 theta angles according to the procedures described herein comprises 2 theta angles (2Θ/°) in at least six positions selected from the above group. In an even further aspect in at least seven positions.

In a further aspect of the invention Form 1 of the compound of Formula (I) as used herein refers to any of:
1) a crystalline compound of Formula (I) characterized by substantially the same XRPD pattern as FIG. 4;
2) a crystalline compound of Formula (I) characterized by substantially the same DSC thermogram as FIG. 5; and/or
3) a crystalline compound of Formula (I) characterized by substantially the same TGA curve as FIG. 6.

In one aspect of the invention, a compound having the Formula (I) is Form 2, characterized by the XRPD pattern expressed in terms of 2 theta angles according to the procedures described herein and shown in FIG. 7. In a further aspect the XRPD pattern expressed in terms of 2 theta angles according to the procedures described herein comprises 2 theta angles (2Θ/°) in at least five positions selected from the group consisting of: 9.1, 9.4, 10.4, 10.9, 11.5, 12.0, 13.0, 13.4, 14.7, 15.4, 15.7, 16.5, 16.8, 18.7, 19.2, 19.5, 19.8 and 20.8 degrees, which correspond respectively to d-spacings at 9.7, 9.5, 8.5, 8.1, 7.7, 7.4, 6.8, 6.6, 6.0, 5.8, 5.6, 5.4, 5.3, 4.7, 4.6, 4.6, 4.5 and 4.3 Angstroms (Å). In a yet further aspect of the invention the XRPD pattern expressed in terms of 2 theta angles according to the procedures described herein comprises 2 theta angles (2Θ/°) in at least six positions selected from the above group. In an even further aspect in at least seven positions.

In a further aspect of the invention Form 2 of the compound of Formula (I) as used herein refers to any of:
1) a crystalline compound of Formula (I) characterized by substantially the same XRPD pattern as FIG. 7;
2) a crystalline compound of Formula (I) characterized by substantially the same DSC thermogram as FIG. 8; and/or
3) a crystalline compound of Formula (I) characterized by substantially the same TGA curve as FIG. 9.

In one aspect of the invention, a compound having the Formula (I) is Form 3, characterized by the XRPD pattern expressed in terms of 2 theta angles according to the procedures described herein and shown in FIG. 10. In a further aspect the XRPD pattern expressed in terms of 2 theta angles according to the procedures described herein comprises 2 theta angles (2Θ/°) in at least five positions selected from the group consisting of: 5.5, 7.3, 7.9, 9.1, 9.5, 10.0, 10.5, 11.0, 11.5, 12.0, 12.6, 14.8, 15.5, 15.8, 16.6, 16.9, 18.2, 18.9 and 19.5 degrees, which correspond respectively to d-spacings at 16.0, 12.1, 11.3, 9.7, 9.4, 8.9, 8.4, 8.1, 7.7, 7.4, 7.0, 6.0, 5.7, 5.6, 5.3, 5.2, 4.9, 4.7 and 4.6 Angstroms (Å). In a yet further aspect of the invention the XRPD pattern expressed in terms of 2 theta angles according to the procedures described herein comprises 2 theta angles (2Θ/°) in at least six positions selected from the above group. In an even further aspect in at least seven positions.

In a further aspect of the invention Form 3 of the compound of Formula (I) as used herein refers to any of:
1) a crystalline compound of Formula (I) characterized by substantially the same XRPD pattern as FIG. 10; and/or
2) a crystalline form of compound of Formula (I) characterized by substantially the same Raman spectrum as FIG. 11.

In a further aspect of the invention Form 4 of the compound of Formula (I) as used herein refers to a crystalline compound of Formula (I) characterized by substantially the same Raman spectrum as FIG. 12.

In a further aspect of the invention Form 5 of the compound of Formula (I) as used herein refers to a crystalline compound of Formula (I) characterized by substantially the same Raman spectrum as FIG. 13.

In a further aspect of the invention Form 6 of the compound of Formula (I) as used herein refers to a crystalline compound of Formula (I) characterized by substantially the same Raman spectrum as FIG. 14.

In a further aspect of the invention Form 7 of the compound of Formula (I) as used herein refers to a crystalline compound of Formula (I) characterized by substantially the same Raman spectrum as FIG. 15.

In a further aspect of the invention Form 8 of the compound of Formula (I) as used herein refers to a crystalline compound of Formula (I) characterized by substantially the same Raman spectrum as FIG. 16.

The compound of the present invention inhibits infiltration of neutrophils into inflamed lung tissue (as demonstrated hereinafter). Therefore this compound has potential utility in acute and chronic treatment of inflammatory pathologies, especially of those pathologies associated with extensive neutrophil infiltration into the lung tissue, for example chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS, known also as adult respiratory distress syndrome or respiratory distress syndrome, RDS), severe or steroid-resistant asthma (Simpson J L et al. (2008) *Am J Respir Crit. Care Med*, 177: 148-155), and emphysema or into the respiratory tract, for example chronic rhinosinusitis (with or without nasal polyposis) (Wallwork B et al. (2006) *Laryngoscope*, 116: 189-193). In addition, the compound of the present invention can be used for the treatment of other diseases associated with altered cellular functionality of neutrophils, for example rheumatoid arthritis (Kitsis E and, Weissmann G, *Clin Orthop Relat Res.* (1991), 265: 63-72), gouty arthritis, inflammatory bowel diseases (such as ulcerative colitis and Chron's disease), glomerulonephritis (Heinzelmann M et al., *Am J Kidney Dis.* (1999), 34(2): 384-399), damage from ischemic reperfusion (Kaminski K A et al., *Int J Cardiol.* (2002), 86(1): 41-59), atherosclerosis (Henriksen P A and Sallenave J M. *Int J Biochem Cell* (2008), 40: 1095-1100), dermatoses such as psoriasis (Terui T et al., *Exp Dermatol.* (2000), 9(1): 1-10) and vasculitis, systemic lupus erythematodes (SLE), systemic inflammatory response syndrome (SIRS), sepsis, ischemia-reperfusion injury, rosacea, periodontitis, gingival hyperplasia and prostatitis syndrome.

"Treating" or "treatment" of neutrophil dominated inflammatory diseases, especially those resulting from neutrophilic infiltration and/or diseases associated with altered cellular functionality of neutrophils means the alleviation of the symptoms and/or retardation of progression of the disease, and may include the suppression of symptom recurrence in an asymptomatic patient.

Inflammatory diseases resulting from neutrophilic infiltration and/or diseases associated with altered cellular functionality of neutrophils include chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In one aspect, the present invention provides a method of treating chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome in a subject in need of such treatment comprising administering to the subject a therapeutically effective amount of the compound of formula (I) or a pharmaceutically acceptable salt thereof.

In one aspect, the present invention provides a method of treating chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis (with or without nasal polyposis) in a subject in need of such treatment comprising administering to the subject a therapeutically effective amount of the compound of formula (I) or a pharmaceutically acceptable salt thereof.

In one aspect, the present invention provides a method of treating chronic obstructive pulmonary disease in a subject in need of such treatment comprising administering to the subject a therapeutically effective amount of the compound of formula (I) or a pharmaceutically acceptable salt thereof.

In a further aspect, the present invention provides a method of treating bronchiolitis obliterans in a subject in need of such treatment comprising administering to the subject a therapeutically effective amount of the compound of formula (I) or a pharmaceutically acceptable salt thereof.

In a further aspect, the present invention provides a method of treating severe or steroid-resistant asthma in a subject in need of such treatment comprising administering to the subject a therapeutically effective amount of the compound of formula (I) or a pharmaceutically acceptable salt thereof.

In a further aspect, the present invention provides a method of treating cystic fibrosis in a subject in need of such treatment comprising administering to the subject a therapeutically effective amount of the compound of formula (I) or a pharmaceutically acceptable salt thereof.

In one aspect, the present invention provides a method of treating chronic rhinosinusitis (with or without nasal polyposis) in a subject in need of such treatment comprising administering to the subject a therapeutically effective amount of the compound of formula (I) or a pharmaceutically acceptable salt thereof.

In one aspect, the present invention provides the compound of Formula (I) or a pharmaceutically acceptable salt thereof for use in medical therapy.

In one aspect, the present invention provides the compound of Formula (I) or a pharmaceutically acceptable salt thereof, for use in the treatment of chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In another aspect, the present invention provides the compound of Formula (I) or a pharmaceutically acceptable salt thereof, for use in the treatment of chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis (with or without nasal polyposis).

In a further aspect, the present invention provides the compound of Formula (I) or a pharmaceutically acceptable salt thereof, for use in the treatment of chronic obstructive pulmonary disease.

In a further aspect, the present invention provides the compound of Formula (I) or a pharmaceutically acceptable salt thereof, for use in the treatment of bronchiolitis obliterans.

In a further aspect, the present invention provides the compound of Formula (I) or a pharmaceutically acceptable salt thereof, for use in the treatment of severe or steroid-resistant asthma.

In a further aspect, the present invention provides the compound of Formula (I) or a pharmaceutically acceptable salt thereof, for use in the treatment of cystic fibrosis.

In a further aspect, the present invention provides the compound of Formula (I) or a pharmaceutically acceptable salt thereof, for use in the treatment of chronic rhinosinusitis (with or without nasal polyposis).

In a further aspect, the present invention provides the use of the compound of Formula (I) or a pharmaceutically acceptable salt thereof in the manufacture of a medicament for the treatment of chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In a further aspect of the invention, the present invention provides the use of the compound of Formula (I) or pharmaceutically acceptable salt thereof in the manufacture of a medicament for the treatment of chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis (with or without nasal polyposis).

In a further aspect, the present invention provides the use of the compound of Formula (I) or pharmaceutically acceptable salt thereof in the manufacture of a medicament for the treatment of chronic obstructive pulmonary disease.

In a further aspect, the present invention provides the use of the compound of Formula (I) or pharmaceutically acceptable salt thereof in the manufacture of a medicament for the treatment of bronchiolitis obliterans.

In a further aspect, the present invention provides the use of the compound of Formula (I) or pharmaceutically acceptable salt thereof in the manufacture of a medicament for the treatment of severe or steroid-resistant asthma.

In a further aspect, the present invention provides the use of the compound of Formula (I) or pharmaceutically acceptable salt thereof in the manufacture of a medicament for the treatment of cystic fibrosis.

In a further aspect, the present invention provides the use of the compound of Formula (I) or pharmaceutically acceptable salt thereof in the manufacture of a medicament for the treatment of chronic rhinosinusitis (with or without nasal polyposis).

The present invention is also directed to compositions comprising the compound of Formula (I) or a pharmaceutically acceptable salt thereof in an amount effective for therapeutic treatment of chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome in a subject in need of such treatment.

In another aspect, the present invention is also directed to compositions comprising the compound of Formula (I) or a pharmaceutically acceptable salt thereof in an amount effective for therapeutic treatment of chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis (with or without nasal polyposis), in a subject in need of such treatment.

The present invention is further related to a pharmaceutical composition for the treatment of chronic obstructive pulmonary disease (COPD), cystic fibrosis (CF), diffuse panbronchiolitis (DPB), bronchiolitis obliterans (BOS), bronchitis, bronchiectasis, acute respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome comprising the compound of Formula (I) or a pharmaceutically acceptable salt thereof.

The present invention is further related to a pharmaceutical composition for the treatment of chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis (with or without nasal polyposis), comprising the compound of Formula (I) or a pharmaceutically acceptable salt thereof.

The benefit to a subject to be treated is either statistically significant or at least perceptible to the subject or to the physician.

"Subject" refers to an animal, in particular a mammal and more particularly to a human or a domestic animal or an animal serving as a model for a disease (e.g., mouse, monkey, etc.). In one aspect, the subject is a human.

A "therapeutically effective amount" means the amount of a compound that, when administered to a subject for treating a neutrophil dominated inflammatory disease resulting from neutrophilic infiltration and/or diseases associated with altered cellular functionality of neutrophils is sufficient to effect such treatment. The "therapeutically effective amount" will vary depending on the disease and its severity and the age, weight, physical condition and responsiveness of the subject to be treated and will ultimately be at the discretion of the attendant physician.

Pharmaceutical Compositions

While it is possible that, for use in the methods of the invention, the compound of Formula (I) or a pharmaceutically acceptable salt thereof may be administered as the bulk substance, it is preferable to present the active ingredient in a pharmaceutical formulation, for example, wherein the agent is in admixture with at least one pharmaceutically acceptable carrier selected with regard to the intended route of administration and standard pharmaceutical practice.

Accordingly, the present invention provides a pharmaceutical composition comprising a) the compound of Formula (I) or a pharmaceutically acceptable salt thereof and b) one or more pharmaceutically acceptable carriers.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise, in addition to the carrier, any suitable binder(s), lubricant(s), suspending agent(s), coating agent(s), and/or solubilizing agent(s).

The phrase "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The present invention is further related to a pharmaceutical composition for the treatment of a neutrophil dominated inflammatory diseases resulting from neutrophilic infiltration and/or diseases associated with altered cellular functionality of neutrophils comprising the compound of Formula (I) or a pharmaceutically acceptable salt thereof.

The present invention is even further related to a pharmaceutical composition comprising a) 10 to 2000 mg of the compound of Formula (I) or a pharmaceutically acceptable salt thereof, and b) 0.1 to 2 g of one or more pharmaceutically acceptable excipients. In a further aspect, the present invention relates to a pharmaceutical composition comprising a) 1 to 2000 mg of the compound of Formula (I) or a pharmaceutically acceptable salt thereof, and b) 0.1 to 2 g of one or more pharmaceutically acceptable excipients.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients. In one aspect, the pharmaceutical composition is formulated for oral administration.

The compound of the invention can be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved, for example, by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of metacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefossé Deutschland GmbH, D-Weil am Rhein, Germany) and other Suppocire type excipients obtained by interesterification of hydrogenated palm oil and palm kernel oil ($C_8$-$C_{18}$ triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and metacrylic acid esters. These latter materials may also be applied to tablets by compression coating.

Pharmaceutical compositions can be prepared by mixing a therapeutically effective amount of the active substance with a pharmaceutically acceptable carrier that can have different forms, depending on the way of administration. Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions (e.g., starch, sugar, kaolin, binders disintegrating agents) preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Pharmaceutical compositions containing the compound of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable flavourings for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

The compound of the invention may also, for example, be formulated as suppositories e.g., containing conventional suppository bases for use in human or veterinary medicine or as pessaries e.g., containing conventional pessary bases.

The compound according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the compound of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and flavourings.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., a hydrofluoroalkane such as 1,1,1,2-tetrafluoroethane (HFA 134AT) or 1,1,1,2,3,3,3-heptafluoropropane (HFA 227EA), or a mixture thereof. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compound according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active compound.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day, 5 and 2000 mg/day, 10 and 2000 mg/day and suitably between about 30 and 1500 mg/day. Other ranges may be used, including, for example, 50-500 mg/day, 50-300 mg/day, 50-100 mg/day, 100-200 mg/day, 5-100 mg/day, 5-50 mg/day. The daily dose as employed for acute or chronic human treatment will range from 0.01 to 250 mg/kg body weight, suitably 0.1-5 mg/kg body weight, suitably 0.1-10 mg/kg body weight, suitably 2-100 mg/kg body weight, or suitably 5-60 mg/kg body weight, which may be administered in one to four daily doses, for example, depending on the route of administration and the condition of the subject. When the composition comprises dosage units, each unit will contain 1 mg to 2 g of active ingredient, suitably 10 mg to 2 g of active ingredient, suitably 200 mg to 1 g of active ingredient, suitably 5 to 300 mg of active ingredient.

Administration may be once a day, twice a day, or more often, and may be decreased during a maintenance phase of the disease or disorder, e.g. once every second or third day instead of every day or twice a day. The dose and the administration frequency will depend on the clinical signs with the reduction or absence of at least one or more, preferably more than one, clinical signs of the acute phase known to the person skilled in the art. In one aspect of the present invention, administration is once daily oral dosing.

In one aspect, the present invention provides a combination comprising a) the compound of Formula (I) or a pharmaceutically acceptable salt thereof and b) one or more further therapeutically active agents.

The combinations referred to above may conveniently be presented for use in the form of a pharmaceutical composition and thus pharmaceutical compositions comprising a combination as defined above together with one or more pharmaceutically acceptable carriers thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Method of Preparation:

The compound of Formula (I) and salts thereof may be prepared by the general methods outlined hereinafter, said methods constituting a further aspect of the invention.

It will be obvious to a person skilled in the art that, in order to avoid interference with any functional groups other than those where structural modifications are to be made, appropriate protection and priority in the synthetic route should be chosen.

The synthesis of the target compound is completed by removing any protecting groups, which are present in the penultimate intermediate using standard techniques, which are well known to those skilled in the art. The deprotected final product is then purified, as necessary, using standard techniques such as silica gel chromatography, HPLC on silica gel, and the like or by recrystallization.

A comprehensive discussion of the ways in which such groups may be protected and methods for cleaving the resulting protected derivatives is given by for example T. W. Greene and P. G. M Wuts in Protective Groups in Organic Synthesis $2^{nd}$ ed., John Wiley & Son, Inc 1991, and by P. J. Kocienski in Protecting Groups, Georg Thieme Verlag 1994. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

The compound of Formula (I) may be prepared by reaction of the compound of Formula (II) wherein $R^1$ is a hydroxy protecting group and $R^2$ is an amino protecting group, with a carboxylic acid or a suitable activated derivative of carboxylic acid of Formula (III), wherein $R^3$ and $R^4$ are each ethyl or are independently a group convertible to ethyl, followed where necessary by subsequent removal of the hydroxyl protecting group $R^1$, the amino protecting group $R^2$, and conversion of the —$NR^3R^4$ group to —$N(CH_2CH_3)_2$.

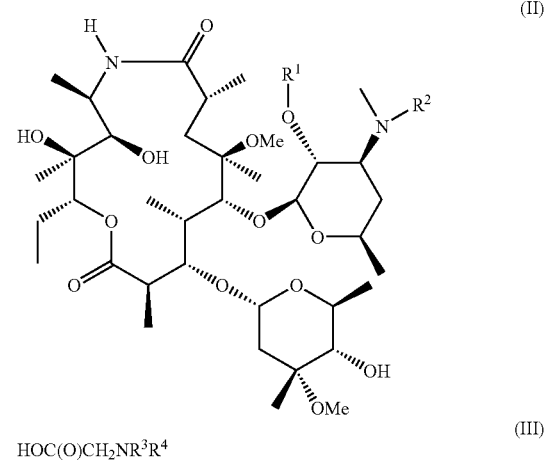

Suitable activated derivatives of Formula (III) include the corresponding acyl halide, mixed anhydride or activated ester such as a thiol ester.

The reaction is preferably carried out in a suitable aprotic solvent such as a halohydrocarbon (e.g. dichloromethane) or N,N-dimethylformamide optionally in the presence of a carbodiimide such as 1-ethyl-3(3-dimethylaminopropyl) carbodiimide hydrochloride, dicyclohexylcarbodiimide, or tertiary base such as 4-(dimethylamino)-pyridine or triethylamine or in the presence of inorganic base (e.g. sodium hydroxide) and at a temperature within the range of 0° to 120° C.

In a further embodiment of the invention, the compound of Formula (I) may also be prepared by reaction of a compound of Formula (IV) wherein L is a suitable leaving group, $R^1$ is a hydroxy protecting group and $R^2$ is an amino protecting group, with an amine of formula (V) wherein $R^3$ and $R^4$ are as defined above for Formula (III).

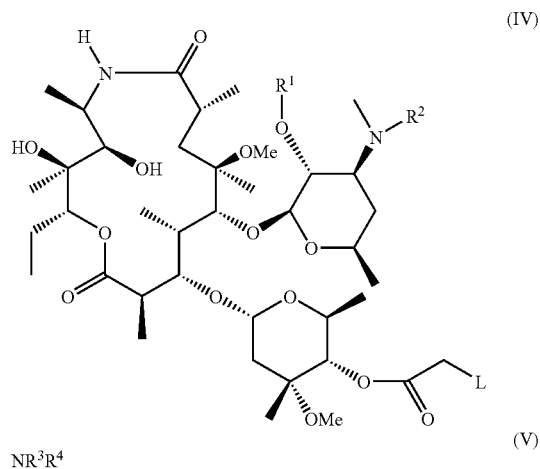

(IV)

$NR^3R^4$ (V)

The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidone and in the presence of a base, followed where necessary by removal of the hydroxyl protecting group $R^1$, the amino protecting group $R^2$, and conversion of the —$NR^3R^4$ group to —$N(CH_2CH_3)_2$. Examples of the bases which may be used include organic bases such as diisopropylethylamine, triethylamine and 1,8-diazabicyclo[5.4.0]undec-7-ene, and inorganic bases such as potassium hydroxide, cesium hydroxide, tetraalkylammonium hydroxide, sodium hydride, potassium hydride and the like. Suitably, L is a halide (e.g. chloride, bromide or iodide) or a sulfonate group (e.g. tosylate, methanesulfonate, or triflate).

Compounds of Formula (II) are known in the art, or may be prepared from the 6-O-methyl-erythromycin A 9(E)-oxime by Beckman rearrangement according to the procedure described in WO99/51616, example 2, page 15 giving 6-O-methyl-9a-aza-9a-homoerythromycin A in a first step, and then by subsequent mono-demethylation of the 3'-$NMe_2$ group by conventional techniques, for example by reaction with iodine under UV radiation (preferably with 500 W halogen lamp), in the presence of sodium acetate trihydrate (U.S. Pat. No. 3,725,385 and WO2004/013153), or by reaction of 6-O-methyl-9a-aza-9a-homoerythromycin A with N-iodosuccinimide in acetonitrile at room temperature (J. Org. Chem. 65 (2000) 3875-3876), or with iodine in presence of morpholine, or by reaction with benzylchloroformate followed by elimination of benzyloxycarbonyl groups at position 2' and 3' as described in U.S. Pat. No. 5,250,518, and by final protection of the hydroxyl group at C/2' and the amino group at C/3'-position by conventional techniques.

Suitably, parallel mono-demethylation of the 3'-$NMe_2$ group and insertion of two benzyloxycarbonyl protective groups at positions C/2'-hydroxyl and 3'-amino may be carried out by reaction of 6-O-methyl-9a-aza-9a-homoerythromycin A with benzylchloroformate, according to the procedure as described in U.S. Pat. No. 5,250,518. Elimination of the benzyloxycarbonyl groups at position 2' and 3' using the procedure as described in U.S. Pat. No. 5,250,518 may be carried out after formation of C/4''-O-(2-diethylaminoethanoyl).

Compounds of Formula (IV) may be prepared by reaction of a compound of Formula (II), with a carboxylic acid or a suitable activated derivative of the carboxylic acid of Formula (VI)

$HOC(O)CH_2L$ (VI)

wherein L is a suitable leaving group as defined above, such as a halide (e.g. chloride, bromide or iodide) or a sulfonate group (e.g. tosylate, methanesulfonate, or triflate). Suitable activated derivatives of the carboxyl group are those defined above for carboxylic acid (III). The reaction is carried out using the conditions described above for the reaction of a compound of Formula (II) with a carboxylic acid of Formula (III).

Compounds of Formula (III), (V) and (VI) are known in the art, or may be prepared by techniques well known in the art.

Pharmaceutically acceptable acid addition salts, which also represent an object of the present invention, may be obtained by reaction of the compound of Formula (I) with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzenesulfonic acid, methane sulfonic acid, laurylsulfonic acid, stearic acid, palmitic acid, succinic acid, ethylsuccinic acid, lactobionic acid, oxalic acid, salicylic acid and similar acid, in a solvent inert to the reaction. Addition salts are isolated by evaporating the solvent or, alternatively, by filtration after a spontaneous precipitation or a precipitation by the addition of a non-polar cosolvent.

Typically, a pharmaceutically acceptable salt may be readily prepared by using a desired acid according to methods known in the art. The salt may precipitate from solution and be collected by filtration or may be recovered by evaporation of the solvent. For example, an aqueous solution of an acid such as hydrochloric acid may be added to an aqueous suspension of the compound of formula (I) and the resulting mixture evaporated to dryness or lyophilised to obtain the acid addition salt as a solid. Alternatively, the compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Assays

The potential for the compound of the present invention to have an advantageous profile for providing therapeutic benefit in the treatment of neutrophil dominated inflammatory diseases resulting from neutrophilic infiltration and/or diseases associated with altered cellular functionality of neutrophils may be demonstrated, for example, using the following assays.

The following abbreviations are used in the text: cfu for colony forming unit, DMSO for dimethyl sulfoxide, LPS for bacterial lipopolysaccharide, PBS for phosphate buffered saline and BAL for bronchoalveolar lavage.
Stability Assays

In Vitro Blood and Plasma Stability Protocol

An in vitro stability study in human whole blood and plasma is carried out over 24 hours at 37° C.

Drug-free freshly collected human blood (CPD—citrate-phosphate-dextrose is used for all blood collections as anti-coagulant) and plasma are spiked with a previously prepared standard solution of test compound to a final concentration of 2000 ng/mL. For each compound blood and plasma are spiked in duplicate and incubated for 24 hours. Two separate aliquots of blood or plasma (50 µL) are sampled from each incubation mixture at 0, 15, 30, 60, 120, 240 and 1440 minutes. All aliquots are mixed with an equal volume of water (50 µL) and extracted with 300 µL of acetonitrile/methanol (2:1) containing internal standard (roxithromycin). The samples are then vortexed, centrifuged and analysed by LC/MS/MS (MRM mode). Results are expressed as the percentage of compound remaining, expressed as the ratio of analyte/internal standard.

Stability in Buffer Solutions and in Bio-Relevant Media Protocol

Stability in buffer solutions pH 2 to pH 8 at 25° C., and in bio-relevant media (SGF pH 1.6, Fasted SIF pH 6.5 and Fed SIF pH 5.0) at 37° C., during 24 hours is monitored. The samples are analysed by LC/MS.
Buffer Solutions and Physiologically Relevant Media Used in Stability Assay:
pH 2—Phosphate buffer
pH 3—Citrate buffer
pH 4—Citrate buffer
pH 5—Citrate buffer
pH 6—Citrate buffer
pH 7—Phosphate buffer
pH 8—TRIS buffer
SGF (Simulated Gastric Fluid) pH 1.6
Fasted SIF (Simulated Intestinal Fluid) pH 6.5
Fed SIF (Simulated Intestinal Fluid) pH 5.0
LC Conditions: Instrument HP1100
Column: Waters XBridge C18, 2.1×50 mm, 3.5 µm
Guard column: Waters XBridge C18, 2.1×10 mm, 3.5 µm
Mobile phase:
   A) 0.1% HCOOH/$H_2O$
   B) 0.1% HCOOH/$CH_3CN$
Gradient Timetable:

| t/min | 0 | 3 | 9 | 9.01 | 10 | 15 |
|---|---|---|---|---|---|---|
| % B | 15 | 30 | 40 | 90 | 15 | 15 |

Flow: 0.3 mL/min
Column temp.: 25° C.
Sample temp.: 25° C. (for stability assay in buffer solutions)
   37° C. (for stability assay in bio-relevant media)
Injector volume: 3 µL (without injection program)
MS Conditions: Instrument HP MS
API-ES, positive ion mode
Mass Range: 150-1500
Fragmentor: 100
Gain: 1.0
Treshold: 150
Step size: 0.20
Gas Temperature: 350° C.
Drying Gas Flow: 13 L/min
Nebulizer Pressure: 35 psig
Capillary Voltage Positive 4000 V
   Negative 4000 V
Sample Preparation:
a) For Stability Assay in Buffer Solutions Compounds are dissolved in $CH_3CN$ to produce a 1 mg/mL stock solution. The stock solution is diluted to a concentration of 0.2 mg/mL (1 mL solution in 4 mL buffer) with appropriate buffer to produce a working solution.

Each solution at each pH is then dispatched into vials that are sealed and stored at room temperature in order to be analyzed at the proper time point. Before analysis, pH values of prepared sample solutions are checked and adjusted if neccessary.
b) For Stability Assay in Bio-Relevat Media
b1) For SGF Media pH 1.6 Testing:

Compounds are dissolved in SGF media pH 1.6 to give 0.2 mg/mL solution in case of compounds 1 and 2, and to give 0.1 mg/mL solution in case of compound 3. Solutions are then stored in a water bath at 37° C. and removed at the proper time point for LC/MS analysis. Before analysis, pH values of prepared sample solutions are checked and adjusted if necessary.
b2) For Fasted SIF Media pH 6.5 Testing:

Compounds are dissolved in Fasted SIF media pH 6.5 to give 2 mg/mL solution. Solutions are then dispatched into vials that are stored in a water bath at 37° C. and removed at the proper time point and diluted 10 times with $CH_3CN$ for LC/MS analysis. Before analysis, pH values of prepared sample solutions are checked and adjusted if necessary.
b3) For Fed SIF Media pH 5.0 Testing:

Compounds are dissolved in Fed SIF media pH 5.0 to give 2 mg/mL solution. Solutions are then dispatched into vials that are stored in a water bath at 37° C. and removed at the proper time point and diluted 40 times with $CH_3CN$ for LC/MS analysis. Before analysis, pH values of prepared sample solutions are checked and adjusted if necessary.

In Vivo Screening Protocols

Lung Neutrophilia Induced by Bacterial Lipopolysaccharide (LPS) in Male BALB/cJ Mice For intraperitoneal administration (i.p.) compounds are dissolved in a final concentration of 10 mg/mL. The required amount of compound is first dissolved in dimethylsulfoxide (DMSO, Sigma) and then diluted with 0.5% (w/v) methylcellulose so that the final DMSO concentration is 5% (v/v). The obtained solution is applied in a dose volume of 0.2 mL per 10 g of animal. Therefore, the compound dose is 200 mg/kg.

Male BALB/cJ mice (Charles River, France), with an average weight of ~30 g are randomly grouped (n=8 in testing group, 10 in positive control and 8 in negative control). Mice receive intraperitoneally (i.p.) a single dose of 200 mg/kg of test compound. Two hours after administration, 2 µg of LPS (from *Escherichia coli* serotype 0111:B4, Sigma), dissolved in sterile PBS in a volume of 60 µL, is intranasally administered to all experimental groups except the negative control group, which receive the same volume of vehicle (PBS). Animals are sacrificed approximately 24 hours after application of LPS in order to obtain bronchioalveolar lavage fluid (BALF), which is used to determine absolute number of cells and the percentage of neutrophils. Results are expressed as percentage decrease in total cell number and number of neutrophils in BALF of treated animals compared to positive control (LPS challenged, but untreated animals).

In Vitro Screening Protocol

Anti-Bacterial Screening

Whole-cell antimicrobial activity of compounds against clinically relevant bacteria (*Staphylococcus aureus* ATCC13709, *Streptococcus pneumoniae* ATCC49619, *Streptococcus pyogenes* ATCC700294, *Moraxella catarrhalis* ATCC23246, *Haemophilus influenzae* ATCC49247 and *Escherichia coli* ATCC25922) is determined by broth microdilution using the Clinical and Laboratory Standards (CLSI) recommended procedure (Document M7-A6A7, Methods for Dilution Susceptibility Tests for Bacteria that Grow Aerobically). Compounds are dissolved in DMSO to produce a 50 mM stock solution. The stock solution is diluted to a concentration of 128 µg/mL in appropriate media (Haemophilus Test Medium for *Haemophilus influenzae*, Mueller-Hinton Broth for *Staphylococcus aureus*, *Moraxella catarrhalis* and *Escherichia coli*, and Mueller-Hinton Broth supplemented with 5% horse serum for *Streptococcus pyogenes* and *Streptococcus pneumoniae*) to produce a working solution. A Tecan Genesis 150 Workstation (Tecan Group Ltd. Mannedorf, Switzerland) is used to prepare serial two-fold dilutions (50 µL aliquots) of the working solution in a U-shape bottom 96 well microtitre plate. After the compounds are diluted, a 50 µL aliquot of the test isolate ($\sim 1 \times 10^6$ cfu/ml) is added to each well of the microtitre plate. The final test concentrations range from 0.125-64 µg/mL. Inoculated plates are incubated at 35° C. in ambient air for 18 to 24 hours. The minimum inhibitory concentration (MIC) is determined as the lowest concentration of compound that inhibited visible growth.

It will be appreciated by a person skilled in the art that the compound of the present invention may have different levels of activity against different strains of the same bacteria.

Cytotoxicity Assay in THP-1 and HepG2 Cell Lines

THP-1 cells are grown in RPMI 1640 medium (Institute of Immunology, Zagreb) supplemented with 10% fetal bovine serum (FBS; BioWest), 50 U/ml penicillin, 50 µg/mL streptomycin, and 2.5 µg/mL amphotericin B (Fungizone) (all from Gibco). HepG2 cells are maintained in Eagle's minimal essential medium (MEM; Gibco) containing 10% FBS, 1 mM sodium pyruvate, 0.1 mM nonessential amino acids, 50 U/mL penicillin, 50 µg/mL streptomycin, and 2.5 µg/mL amphotericin B (Fungizone) (all from Gibco).

To determine whether the anti-inflammatory activity of the test compounds is due to observed inhibition of cytokine production and is not a consequence of cellular cytotoxicity, measurement of succinate dehydrogenase activity in living cells is performed. Cells are cultured for 24 h in appropriate tissue culture medium in the presence of the test compounds at concentrations of 100, 50, 25, 12.5, 6.25, 3.13, 1.56, 0.78 µM. MTT [3-(4,5-dimethylthiazole-2-yl)-2,5-diphenyl tetrazolium bromide] (Promega, USA), a detection reagent, is then added and the cultures are incubated for 0.5-2 h. The amount of MTT-formazan produced is determined using a spectrophotometer at 492 nm (Mosmann, *J. Immunol. Methods*, (1983) 65: 55-63).

The percentage of inhibition of cell growth is calculated using the following formula:

% inhibition of cell growth=$OD_{492}$ treated cells/$OD_{492}$ nontreated cells×100.

EXAMPLES

The following abbreviations are used in the text: EtOAc for ethyl acetate, DCM for dichloromethane, EDCxHCl for 1-ethyl-3(3-dimethylaminopropyl) carbodiimide hydrochloride, DMAP for 4-(dimethylamino)-pyridine, EtOH for ethanol, EtOAc for ethyl acetate, DMSO for dimethyl sulfoxide, MeOH for methanol, TEA for triethylamine, DEA for diethylamine, MTBE for methyl tert-butyl ether, i-PrOH for isopropanol and iPrOAc for isopropylacetate.

The compounds and processes of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

In the procedures that follow, reference to the product of an Intermediate or Example by number is typically provided. This is provided merely for assistance to the skilled chemist to identify the starting material used. The starting material may not necessarily have been prepared from the batch referred to.

6-O-methyl-9a-aza-9a-homoerythromycin A can be prepared according to procedure of WO99/51616, example 2, page 15.

Polymorphic forms of the compound of Formula (I) may be characterized and differentiated using a number of conventional analytical techniques, including but not limited to X-ray powder diffraction (XRPD), Raman spectroscopy, differential scanning calorimetry (DSC), thermogravimetric analysis (TGA), and nuclear magnetic resonance spectroscopy (NMR). These techniques may be employed alone or in combination with other techniques to characterize a sample and to distinguish one form from the other of the compound of Formula (I).

X-Ray Powder Diffraction (XRPD)

The X-ray powder diffraction (XRPD) data were acquired on a PANalytical X'Pert Pro powder diffractometer, model PW3040/60, using an X'Celerator detector. The acquisition conditions were:

a) radiation: Cu Kα, generator tension: 45 kV, generator current: 40 mA, start angle: 3.0°2θ, end angle: 40.0°2θ, step size: 0.0167°2θ, time per step: 104.7 seconds; or b) radiation: Cu Kα, generator tension: 40 kV, generator current: 45 mA, start angle: 2.0°2θ, end angle: 40.0°2θ, step size: 0.0167°2θ, time per step: 31.75 seconds.

The sample was prepared by mounting a few milligrams of sample on a Si wafer (zero background) plate, resulting in a thin layer of powder for analysis. Some margin of error is present in each of the 2 theta angle assignments and d-spacings.

The margin of error will be dependant on a number of factors, including the exact temperature at which the values are measured. The margin of error in the foregoing 2 theta angles is approximately ±0.2 degrees for each of the foregoing peak assignments. Since some margin of error is possible in the assignment of 2 theta angles and d-spacings, a useful method of comparing XRPD patterns in order to identify the particular form of a sample of the compound of Formula (I) is to overlay the XRPD pattern of the one sample form of the compound of Formula (I) over the XRPD pattern of the other sample form of the compound of Formula (I).

Raman Spectroscopy

All Raman analyses were performed on a Kaiser Optical Systems HoloWell dispersive Raman spectrometer with an automated XYZ stage. Excitation was provided by a diode laser at 785 nm. Approximately 5-20 mg of sample was placed on borosilicate fritted plates or within a glass sample vial. Slight variations in observed Raman peaks are expected based on the specific spectrometer employed and the analyst's sample preparation technique. The margin of error in the forgoing band positions is ±2 cm$^{-1}$. The Raman spectra provided herein show at the x-axis wavenumbers in cm$^{-1}$ and at the y-axis intensity in arbitrary units.

Differential Scanning Calorimetry (DSC)

DSC was performed on a Mettler Toledo DSC 822e calorimeter equipped with a refrigerated cooling system. The sample was heated in a pin-holed aluminium pan at a heating rate of 10° C./minute from 25° to 300° C. A nitrogen purge at 50 mL/min was maintained over the sample.

Significant variations in the observed endotherms are expected in respect of the DSC thermogram of each of the forms of the compound of Formula (I), based on the specific instrument and pan configuration employed, the analyst's sample preparation technique, and the sample particle size and weight. Some margin of error is normally present in the endotherm characteristics, i.e. the margin of error is approximately in the order of ±2.00° C.

Thermogravimetric Analysis (TGA)

TGA was performed on a Mettler Toledo TGA/SDTA 851e system. The sample was loaded onto a pre-tared alumina crucible, and was heated at a heating rate of 10° C./minute from 25° to 300° C. A nitrogen purge at 50 ml/min was maintained over the sample.

Example 1

3'-N-Demethyl-4''-O-(2-diethylaminoethanoyl)-6-O-methyl-9a-aza-9a-homoerythromycin A Method A

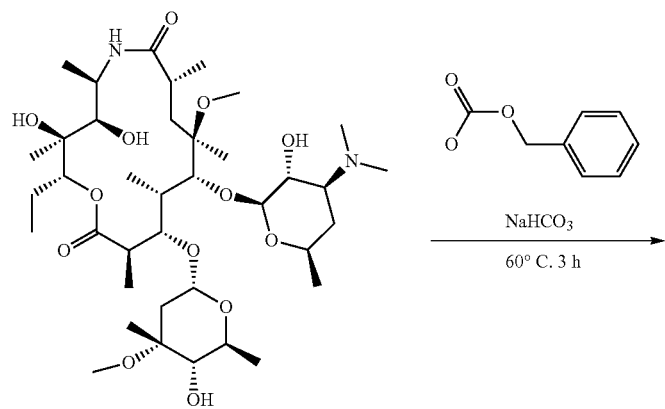

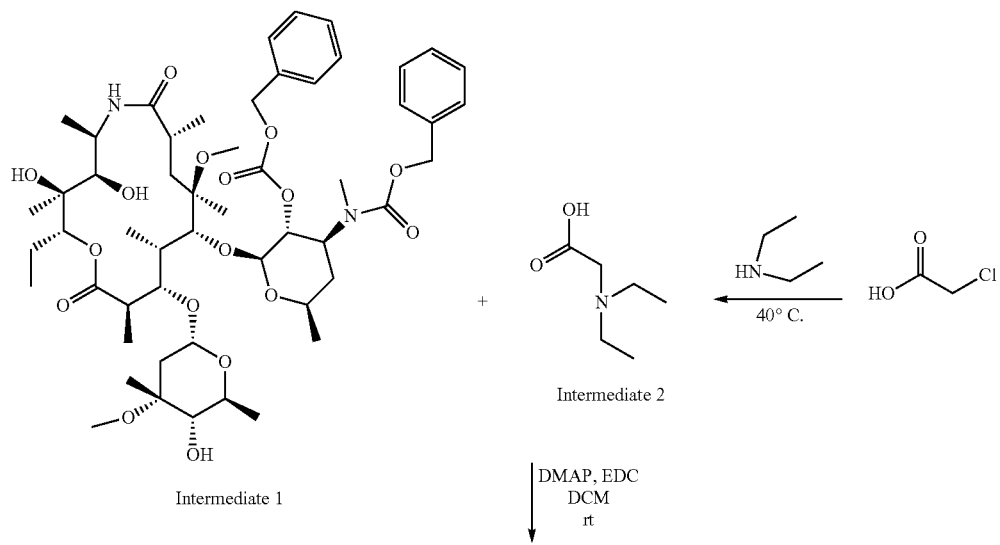

Intermediate 1

Intermediate 2

DMAP, EDC
DCM
rt

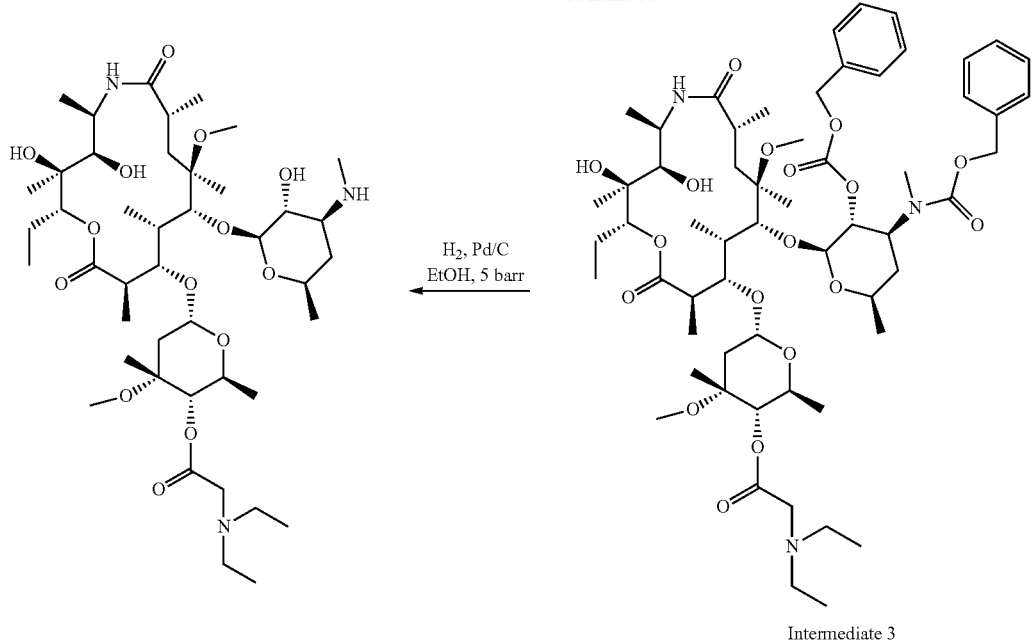

Intermediate 3

Intermediate 1:

3'-N-Demethyl-2'-O-3'-N-di-{[(phenylmethyl)oxy]carbonyl}-6-O-methyl-9a-aza-9a-homoerythromycin A To the heated (60° C.) suspension of NaHCO$_3$ (13.2 g, 157.3 mmol) in benzylchloroformate (30 mL, 209.7 mmol), 6-O-methyl-9a-aza-9a-homoerythromycin A (10 g, 13.1 mmol) was gradually added during 2 h. The reaction mixture was stirred at 60° C. for additional 1 h. The reaction mixture was then cooled to room temperature, hexane (150 mL) and water (150 mL) were added and the obtained sticky precipitate was filtered off, dissolved in EtOAc (150 mL) and washed with water (2×100 mL). After drying over anhydrous Na$_2$SO$_4$ the organic layer was evaporated, to the residue diethyl ether (80 mL) was added and the product precipitated by addition of hexane (200 mL) under ice cooling. The obtained precipitate was filtered and washed with cold hexane (50 mL) to afford title Intermediate 1 (12.7 g), MS (ES+) m/z: 1039.28 [MH+Na]+.

Intermediate 2:

Diethylaminoacetic Acid

A solution of chloroacetic acid (30 g, 0.32 mol) in diethylamine (230 mL, 2.2 mol) was stirred overnight. The obtained white precipitate was removed by filtration. The filtrate was evaporated to dryness to afford yellow oil to which EtOAc (300 mL) was added. The obtained precipitate was again removed by filtration. The filtrate was evaporated to afford yellow solid residue (44 g) that was washed with hexane (2×100 mL), EtOAc (2×50 mL) and again with hexane (50 mL), and then dried in vacuo to afford title Intermediate 2 (38 g).

$^1$H NMR (500 MHz, CHLOROFORM-d) δ ppm 8.85 (1H, br.$), 3.56 (2H, s), 3.29 (4H, q, J=7.3 Hz), 1.36 (6H, t, J=7.3 Hz).

Intermediate 3:

3'-N-Demethyl-4"-O-(2-diethylaminoethanoyl)-2'-O-3'-N-di-{[phenylmethyl)oxy]carbonyl}-6-O-methyl-9a-aza-9a-homoerythromycin A To a solution of Intermediate 1 (12.7 g, 12.5 mmol) in DCM (35 mL), EDC×HCl (14.4 g, 74.9 mmol), DMAP (9.15 g, 74.9 mmol), and Intermediate 2 (diethylaminoacetic acid) (9.83 g, 74.9 mmol) were added. Reaction mixture was stirred overnight (approximately 17 hours) at room temperature, diluted with EtOAc (450 mL) and washed with saturated NaHCO$_3$ (3×170 mL), saturated NH$_4$Cl (3×170 mL), and brine (350 mL). The organic phase was dried over anhydrous Na$_2$SO$_4$, solvent was evaporated, the residue suspended in petrolether (250 mL), stirred for 2 hours, and filtrated, washed with petrolether (30 mL), to afford title Intermediate 3 (12.2 g), MS (ES+) m/z: 1130.39 [MH]+.

3'-N-Demethyl-4"-O-(2-diethylaminoethanoyl)-6-O-methyl-9a-aza-9a-homoerythromycin A Method 1. To a solution of Intermediate 3 (12.2 g, 10.8 mmol) in EtOH (200 mL), 10% Pd/C (1.22 g) was added and the reaction mixture was hydrogenolized at 5 barr overnight (approximately 17 hours). Catalyst was removed by filtration and filtrate evaporated. To the residue DCM (200 mL) and water (200 mL) were added and the pH adjusted (1N HCl) to 4.7. The layers were separated, and extraction at pH 4.7 repeated with DCM (3×150 mL). To the water layer fresh DCM (150 mL) was added and the pH adjusted (1N NaOH) to 5.7. The layers were separated and extraction at pH 5.7 repeated with DCM (2×20 mL, 7×150 mL). Combined organic layers at pH 5.7 were concentrated to volume of 150 mL, water (150 mL) was added and pH adjusted (water/NH$_4$OH=1/1) to 9.5. Organic layer was separated and evaporated to afford the title product Example 1 (7.25 g, MS (ES+) m/z: 862.34 [MH]+).

Method 2. To a solution of Intermediate 3 (11.52 g, 10.2 mmol) in EtOH (200 mL), 10% Pd/C (1.15 g) was added and the reaction mixture was hydrogenolized at 5 barr overnight (approximately 17 hours). Catalyst was removed by filtration and filtrate evaporated. The residue was dissolved in acetone (25 mL) and the product precipitated by addition of petrolether (250 mL) to afford title product (6.9 g) which was further re-crystallized from acetonitrile to afford title product (4.36 g). Evaporation of mother liquor and re-precipitation afforded additional amount of the title product Example 1 (2.27 g).

MS (ES+) m/z: 862.11 [MH]+.

$^1$H NMR (500 MHz, CHLOROFORM-d) δ ppm 6.12 (1H, d, J=8.2 Hz), 4.88 (1H, d, J=4.9 Hz), 4.72 (1H, d, J=9.8 Hz), 4.68 (1H, dd, J=10.7, 1.5 Hz), 4.55 (1H, d, J=7.6 Hz), 4.39 (1H, m), 4.21 (1H, dd, J=6.1, 1.5 Hz), 4.16 (1H, m), 3.79 (1H, m), 3.74 (1H, d, J=6.4 Hz), 3.43 (1H, d, J=17.2 Hz), 3.31 (3H, s), 3.31 (3H, s), 3.31 (1H, d, J=17.1 Hz), 3.28 (1H, d, J=4.3 Hz), 3.21 (1H, br. s), 3.14 (1H, dd, J=9.8, 7.3 Hz), 2.83 (1H, m), 2.69 (4H, q, J=7.3 Hz), 2.59 (1H, ddd, J=11.5, 9.8, 4.6 Hz), 2.43 (3H, s), 2.37 (1H, d, J=15.0 Hz), 2.22 (1H, dq, J=7.3, 7.1 Hz), 2.01 (1H, dd, J=15.0, 8.2 Hz), 1.89 (3H, m), 1.62 (1H, dd, J=15.0, 4.9 Hz), 1.56 (1H, m), 1.33 (3H, s), 1.29 (1H, d, J=13.7 Hz), 1.24 (3H, d, J=7.6 Hz), 1.16 (12H, m), 1.12 (3H, s), 1.09 (4H, d, J=7.1 Hz), 1.07 (6H, t, J=7.3 Hz), 0.98 (3H, d, J=7.6 Hz), 0.90 (3H, t, J=7.5 Hz).

Method B

Intermediate 1:

3'-N-Demethyl-2'-O-3'-N-di-{[(phenylmethyl)oxy]carbonyl}-6-O-methyl-9a-aza-9a-homoerythromycin A Step a) 6-O-methyl-9a-aza-9a-homoerythromycin A 6-O-methyl erythromycin A 9(E)-oxime (2.0 kg) was charged into a 50 L glass-lined reactor followed by acetone (20 L). The mixture was cooled to −10° C. and toluene-2-sulfonyl chloride (775 g, 1.55 eq) in acetone (5.5 L) was added during 20 minutes. The temperature during addition rose to −8° C. Then NaHCO$_3$ (460 g) in water (25 L) was added drop wise during 1 hour 40 min, keeping the internal temperature below 0° C. Mixture was warmed to 20° C. and stirred for 2 hours, then 1M KOH (6 L) was added. The heating jacket was set to 70° C. and the reaction volume was reduced in vacuo to ~18 L. The mixture was cooled to 10° C. and filtered on nutsche (seitz K200 filter), filter cake washed with water (8 L). The heavy off-white precipitate was air-dried on filter over night then in vacuo at 32° C. to afford title product (1670 g, Y=83.5%, LC-MS purity conforms to reference).

Step b) 3'-N-Demethyl-2'-O-3'-N-di-{[(phenylmethyl)oxy]carbonyl}-6-O-methyl-9a-aza-9a-homoerythromycin A Batch A 6-O-Methyl-9a-aza-9a-homoerythromycin A (1.01 kg) was charged into a 20 L reactor followed by dioxane (4 L) and NaHCO$_3$ (1.49 kg). The jacket temperature was set to 90° C. When the internal temperature reached 72° C., addition of benzyl chloroformate (800 mL, 4.4 equiv. also known as carbobenzoxy chloride or phenylmethyl chloroformate) started and continued for 4 hours 10 min. After 30 min extra benzyl chloroformate (30 mL) was added. Full conversion was confirmed by LC-MS, and the mixture was cooled to 20° C., diluted with MTBE (6 L) and quenched with 0.01 M KOH (5 L) and stirred over night. The aqueous layer was removed, the organic layer was washed with water (2×5 L) and brine (2 L). The volume of the organic layer was ~7 L, and the solution was transferred into an addition funnel. Heptane (14 L) was charged into the reactor and cooled down to 10° C. Then, MTBE solution from the addition funnel was added carefully to the stirred heptane. After ca ⅔ of solution was added suspended particles started to form a coagulate resulting in sticky oil on the bottom of the reactor. After almost all heptane was removed, MTBE (1 L) and DCM (5 L) were added until everything dissolved. Obtained solution was added to the Batch B.

Batch B: Dioxane (11 L) was charged into a 50 L reactor followed by 6-O-methyl-9a-aza-9a-homoerythromycin A (2.7 kg) and NaHCO$_3$ (4.0 kg). The jacket was set to 85° C. and when the internal temperature reached 70° C., addition of benzyl chloroformate (2.25 L, 4.5 equiv. also known as carbobenzoxy chloride or phenylmethyl chloroformate) started and continued over 8 hours. Then extra benzyl chloroformate (50 mL) was added. Full conversion was confirmed by LC-MS, and the mixture was cooled to 20° C., diluted with MTBE (15 L) and quenched with 0.01 M KOH (15 L) and left over weekend. The aqueous layer was removed, the organic layer was washed with water (2×15 L) and brine (10 L), and combined with solution from Batch A. The volume was reduced in vacuo to ~10 L, and the solution was transferred into an addition funnel. Heptane (45 L) was charged into the reactor and cooled down to 10° C. Then, MTBE solution was added carefully to well agitated heptane during 10 min. The resulting white amorphous precipitate was filtered by a nutsche (seitz K200 filter), washed with heptane (2×5 L) and air-dried on filter for 48 hours to afford title product (5.8 kg, LC-MS purity conforms to reference). The wet material was used in the next reaction step without further work-up.

Intermediate 2:

Diethylaminoacetic Acid

Diethylamine (9.5 L) was charged into a 20 L glass-lined reactor and cooled to 3° C. Chloroacetic acid (1.21 kg) in MTBE (1.8 L) was added over 1 hour with cooling—the temperature rose to 16° C. during the addition. The mixture was warmed to 20° C., stirred over night and concentrated on rotary evaporator giving yellow oil. This oil was re-concentrated with iPrOAc, mixed with iPrOAc (4.5 L) and stirred over night. The off-white hygroscopic precipitate was filtered, washed with iPrOAc (1.5 L) and immediately placed into a drying cabinet to avoid deliquescence. After drying, titled product was obtained (820 g, Y=49%).

Intermediate 3:

3'-N-Demethyl-4"-O-(2-diethylaminoethanoyl)-2'-O-3'-N-di-{[(phenylmethyl)oxy]carbonyl}-6-O-methyl-9a-aza-9a-homoerythromycin A DCM (10 L) was charged into the 50 L glass-lined reactor and internal temperature adjusted to +5° C. All reagents were then charged in one portion in the following order: 3'-N-demethyl-2'-O-3'-N-di-{[(phenylmethyl)oxy]carbonyl}-6-O-methyl-9a-aza-9a-homoerythromycin A (2800 g, wet material), diethylaminoacetic acid (800 g, 2.2 eq), DMAP (745 g, 2.2 eq) and EDC×HCl (1170 g, 2.2 eq). This resulted in an endothermic temperature decrease to +2° C. The mixture was stirred overnight at +20° C., cooled to +10° C., quenched with saturated aqueous NaHCO$_3$ (20 L), and stirred for 0.5 hour. EtOAc was added (25 L), aqueous layer was separated and discarded, organic layer washed with saturated aqueous NH$_4$Cl (2×12 L) and brine (10 L). Volume was reduced in vacuo to ~8 L. Heptane (45 L) was charged into a second reactor and cooled down to 8-10° C. The DCM/EtOAc concentrated solution was added carefully to cooled heptane over 20 minutes with good agitation. The resulting white amorphous precipitate was filtered on nutsche (seitz K200 filter), washed with heptane (8 L) and air-dried on the filter overnight to afford crude title product (2.5 kg, Y=79%, LC-MS profile conforms to reference).

The crude solid (2.38 kg) was dissolved in refluxing MTBE (18.3 L) at 50° C., and heptane (15 L) was added slowly over 20 minutes keeping internal temperature around 50° C. The mixture was seeded, allowed to cool to 20° C. and stirred overnight. White precipitate was filtered, washed with MTBE/heptane 1:1 (5 L), then pure heptane (3 L) and air-dried 24 hours to afford title product (1.9 kg, Y=63%, LC-MS profile conforms to reference, LC purity 98.5%).

3'-N-Demethyl-4''-O-(2-diethylaminoethanoyl)-6-O-methyl-9a-aza-9a-homoerythromycin A 3'-N-Demethyl-4''-O-(2-diethylaminoethanoyl)-2'-O-3'-N-di-{[(phenylmethyl)oxy]carbonyl}-6-O-methyl-9a-aza-9a-homoerythromycin A (1.9 kg) was dissolved in MeOH (16 L) and resulting solution was charged into a 20 L autoclave followed by addition of 10% Pd/C (150 g, wet 60% $H_2O$) in MeOH (0.5 L). The autoclave was evacuated and filled with hydrogen (repated two times in order to remove all residual oxygen). After refiling the autocalve with hydrogen the mixture was hydrogenolized at 1.5-3 bar for 10 hours. The Pd/C was filtered off via celite and the cake was washed with MeOH (1 L). Resulting solution was charged into 50 L reactor, Pd scavenger (Biotage MP-TMT, 50 g) added and the mixture was stirred at the room temperature overnight. Then mixture was filtered, transferred in plastic container and stored at –10° C. After that MeOH mixture was transferred to reactor and concentrated almost to dryness, Then EtOAc charged (12.5 L) followed by water (10 L) and 1M HCl solution (3 L). The organic phase was separated and discarded. To the aqueous phase solid $NaHCO_3$ (280 g) and EtOAc (10 L) were added, brine (1 L) was added to achieve separation. After layers were separated, the product was extracted with EtOAc (2×7 L), combined organic phases concentrated in vacuo almost to dryness, diluted with heptane (2 L) and again concentrated. Then diethyl ether (7 L) was added, mixture stirred 3.5 hours, white precipitate filtered, washed with around 2 L of diethyl ether, and air-dried over night to afford the title product Example 1 (946 g, Y=65%, $^1$H NMR profile conforms to reference, with the difference in chemical shifts of several protons located around C/3'-$NHCH_3$, which suggests partial HCl salt formation, HPLC purity 97.8%).

A considerable amount of precipitate remained in the reactor. It was dissolved in MeOH, and concentrated on rotary evaporator. Obtained oily residue was slurried in diethyl ether (2 L), stirred 3 hours, filtered, washed with diethyl ether (300 mL) and air-dried overnight giving additional amount of the crude title product (250 g, Y=17%).

Freebasing was achieved using either aqueous ammonia or using saturated $NaHCO_3$ solution:

The product (20 g, 10 g of partial HCl salt+10 g of crude material) was dissolved in DCM (150 mL), mixed with either aqueous ammonia solution (12.5%, 100 mL) or with saturated $NaHCO_3$ solution (100 mL) and stirred for 1.5 hours. Layers were separated, and the aqueous layer extracted with additional DCM (75 mL). Combined organic layers were concentrated almost to dryness, slurried in diethyl ether (100 mL), volume reduced slightly (to about 90 mL), which resulted in slow precipitation of the 3'-N-Demethyl-4''-O-(2-diethylaminoethanoyl)-6-O-methyl-9a-aza-9a-homoerythromycin A, Form 1 (the XRPD pattern conformed with the XRPD pattern of Example 11, Form 1).

Method C

Intermediate 1:

3'-N-Demethyl-2'-O-3'-N-di-{[phenylmethyl)oxy]carbonyl}-6-O-methyl-9a-aza-9a-homoerythromycin A Step a) 6-O-methyl-9a-aza-9a-homoerythromycin A To a solution of 6-O-methyl erythromycin A 9(E)-oxime (12.00 kg) in acetone (72.0 L) which was cooled to 2.5±2.5° C., solution of $NaHCO_3$ (3.3 kg) in water (120.0 L) was added during 2 hours and temperature kept at 2.5±2.5° C. A solution of p-toluene sulfonyl chloride (4.79 kg) in acetone (12.0 L) was added to this mixture within 15 minutes under cooling, and than warmed to the ambient temperature (1 hour 15 minutes) and stirred for 2 hours. The reaction mixture was divided into two halfs (cca 102.0 L), each of which was transferred to a new reactor, to each half water (96.0 L) was added, reaction mixture cooled to 7.5±2.5° C. during cca 1.5 hour. Then to each half pH was adjusted to pH 9.0-11.5 by addition of 10.0 L of previously prepared aqueous solution of NaOH (1.80 kg in 36.0 L of water) during about 1 hour. The resulting suspension was aged at 7.5±2.5° C. for 2 hours, isolated by centrifuge filtration and washed with water three times (24.0 L, 48.0 L and 24.0 L) to afford wet product (13.50 kg). The wet product was dried at 40±5° C. under vacuum for 10 hours to afford the title product (10.82 kg, $^1$H NMR profile conforms to reference).

Step b) 3'-N-Demethyl-2'-O-3'-N-di-{[(phenylmethyl)oxy]carbonyl}-6-O-methyl-9a-aza-9a-homoerythromycin A Batch A Dioxane (40.0 L) was charged to the reactor, temperature set at 30±5° C., 6-O-methyl-9a-aza-9a-homoerythromycin A (8.00 kg) followed by $NaHCO_3$ (10.56 kg) were added. To this mixture benzyl chloroformate (9.00 kg) was slowly added during 30 minutes at 30±5° C. After addition, the mixture was heated to 60±5° C. and maintained for 2.5 hours. The reaction mixture was transferred to a new reactor, cooled to 7.5±7.5° C., diluted with MTBE (80.0 L), and then treated with triethylamine (8.0 L) slowly at 7.5±7.5° C. A pre chilled 0.01N potassium hydroxide solution (4.035 kg in 60.0 L of water) was added to the above reaction mixture at 7.5±7.5° C. and stirred for 10 minutes at 12.5±2.5° C. The layers were separated and the upper organic layer was washed with water twice (2×40.0 L) and then with aqueous sodium chloride solution (8.00 kg in 40.0 L) while maintaining temperature at 12.5±5° C.

The organic layer was concentrated under high vacuum (NLT 650 mm/Hg) at below 60° C. until no distillate was observed. MTBE (16.0 L) was added to the residue and stirred at 32.5±7.5° C. to give a solution. The obtained solution was transferred to an addition vessel and slowly added to hexane (160.0 L) over 1 hour at 30±5° C., rinsing the addition vessel with MTBE (4.0 L). The mixture was stirred for 45 minutes at 30±5° C., cooled to 2.5±2.5° C., aged for 90 minutes and isolated by centrifuge filtration. The cake was washed with hexane (16.0 L) and dried under vacuum at 30±5° C. for 5 hours to afford crude solid product.

The crude solid was suspended in mixture of MTBE (16.0 L) and triethylamine (8.0 L), heated at 65±10° C. for 12 hours before cooling to ambient temperature and diluting with further MTBE (16.0 L). The slurry was aged at ambient temperature for further 12 hours before isolation by centrifuge filtration. The cake was washed with MTBE (16.0 L) and dried under vacuum at 30±5° C. for 10 hours to afford the title product (6.95 kg).

Batch B Dioxane (50.0 L) was charged to the reactor, temperature set at 30±5° C., 6-O-methyl-9a-aza-9a-homoerythromycin A (10.00 kg) followed by NaHCO₃ (13.21 kg) were added. To this mixture benzyl chloroformate (11.25 kg) was slowly added during 30 minutes at 30±5° C. After addition, the mixture was heated to 60±5° C. and maintained for several hours (4 hours). The reaction mixture was transferred to a new reactor, cooled to 7.5±7.5° C., diluted with MTBE (100.0 L), and then treated with triethylamine (10.0 L) slowly at 7.5±7.5° C. A pre chilled 0.01N potassium hydroxide solution (0.044 kg in 75.0 L of water) was added to the above reaction mixture at 7.5±7.5° C. and stirred for 15 minutes at 12.5±2.5° C. The layers were separated and the upper organic layer was washed with water twice (2×50.0 L) and then with aqueous sodium chloride solution (10.00 kg in 50.0 L of water) while maintaining temperature at 12.5±2.5° C.

The organic layer was concentrated under high vacuum (NLT 650 mm/Hg) at below 60° C. until no distillate was observed. MTBE (20.0 L) was added to the residue and stirred at 32.5±7.5° C. to give a solution. The obtained solution was transferred to an addition vessel and slowly added to hexane (200.0 L) over 1 hour 20 minutes at 30±5° C., rinsing the addition vessel with MTBE (5.0 L). The mixture was stirred for 30 minutes at 30±5° C., cooled to 2.5±2.5° C., aged for 90 minutes and isolated by centrifuge filtration. The cake was washed with hexane (20.0 L) and dried under vacuum at 30±5° C. for 5 hours to afford crude solid product.

The crude solid was suspended in mixture of MTBE (20.0 L) and triethylamine (10.0 L), heated at 65±10° C. for 9 hours before cooling to ambient temperature and diluting with further MTBE (20.0 L). The slurry was aged at ambient temperature for further 10 hours before isolation by centrifuge filtration. The cake was washed with MTBE (15.0 L) and dried under vacuum at 65±10° C. for 8 hours to afford the title product (8.75 kg).
Intermediate 2:

Diethylaminoacetic Acid

Diethylamine (112.0 L) was charged into reactor and cooled to 2.5±2.5° C. Chloroacetic acid (14.00 kg) was added portionwise during 30 minutes while temperature kept at 5±5° C. The mixture was warmed to 30±5° C. during 1 hour and than stirred at the same temperature over night (about 17 hours). Reaction mixture was filtered through Nuche filter and filtrate collected to a dry container. The cake was washed with ethyl acetate (28.0 L) and filtrate collected in a dry container.

Ethyl acetate (70.0 L) was charged to a reactor, wet cake was added and slurried at 30±5° C. for 20 minutes. The slurry was filtered through Nutsche filter and filtrate collected to a dry container. The cake was washed with ethyl acetate (28.0 L) and filtrate collected in the dry container.

Combined collected filtrates were charged into the new reactor, solvent was distilled out under vacuum at below 60° C. until no distillate was observed. Residue was cooled to 30±5° C., mixture of acetonitrile (14.0 L) and acetone (28.0 L) was added and stirred at 25±2° C. for 11 hours. The obtained hygroscopic precipitate was filtrated under nitrogen flow. The wet cake was washed with acetone (20.0 L), dried under vacuum (650 mmHg) at 45±5° C. for about 1.5 day to afford title product (4.32 kg).
Intermediate 3:

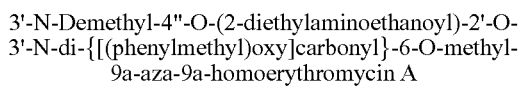

3'-N-Demethyl-4"-O-(2-diethylaminoethanoyl)-2'-O-3'-N-di-{[(phenylmethyl)oxy]carbonyl}-6-O-methyl-9a-aza-9a-homoerythromycin A DCM (40.0 L) was charged into the reactor and temperature adjusted to 30±5° C., 3'-N-demethyl-2'-O-3'-N-di-{[(phenylmethyl)oxy]carbonyl}-6-O-methyl-9a-aza-9a-homoerythromycin A (8.0 kg) was added and stirred until clear solution was observed. Then, under stirring and keeping temperature at 30±5° C. diethylaminoacetic acid (1.55 kg), followed by DMAP (0.96 kg) were added. The reaction mixture was cooled to 2.5±2.5° C. EDC×HCl (1.50 kg) was added at this temperature to give a clear solution. The reaction mixture was slowly warmed to 25±5° C. and stirred for 5 hours at 25±5° C. Further DMAP (1.20 kg) was added and the reaction was again cooled to 2.5±2.5° C. Further EDC×HCl (1.88 kg) was added at this temperature to give a clear solution. The reaction mixture was slowly warmed to 25±5° C. and stirred for 11 hours at 25±5° C. The mixture was then concentrated under vacuum at below 30° C. till no distillate was observed, the residue was dissolved in toluene (80.0 L) and the mixture was cooled to 15±5° C. The organic solution was washed twice with aqueous sodium bicarbonate (4.00 kg in 40.0 L of water), retaining the aqueous layer after each extraction at 15±5° C. The upper organic layer was washed twice with aqueous ammonium chloride (12.00 kg in 40.0 L of water), retaining the aqueous layer after each extraction at 10-15° C. The combined aqueous washes (sodium bicarbonate and ammonium chloride) were back-extracted with toluene (40.0 L), and the organic layer was washed sequentially with aqueous sodium bicarbonate (4.00 kg in 40.0 L of water) and aqueous ammonium chloride (12.00 kg in 40.0 L of water).

The combined organic phases were washed with aqueous sodium chloride (12.00 kg in 40.0 L of water), and the organic layer was dried over anhydrous sodium sulphate, filtered through a Nutsche filter and washed with toluene (16.0 L). The combined filtrates and washing were concentrated under vacuum at below 50° C. to till approximately 5.0-5.5 volume left inside the reactor. Heptane (80.0 L) was added slowly over 30 minutes at 35±5° C. and the resulting suspension was stirred for 13 hours at 30±5° C. The product was isolated by centrifuge filtration and washed with heptane (16.0 L). The product was dried under high vacuum (NLT 650 mm/Hg) at 40±5° C. for 11 hours to afford the title product (7.30 kg).

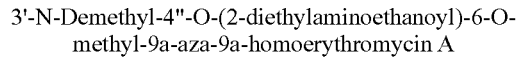

3'-N-Demethyl-4"-O-(2-diethylaminoethanoyl)-6-O-methyl-9a-aza-9a-homoerythromycin A The reactor was evacuated and rinsed with nitrogen (repeated two times), Under the nitrogen flow i-PrOH (36.0 L)

and 3'-N-demethyl-4"-O-(2-diethylaminoethanoyl)-2'-O-3'-N-di-{[(phenylmethyl)oxy]carbonyl}-6-O-methyl-9a-aza-9a-homoerythromycin A (4.5 kg) were added and solution stirred for 10 minutes. Then, 10% Pd/C (0.225 kg) followed by triethylamine (1.80 L) were added, nitrogen flow was stopped, reactor evacuated and filled with hydrogen till 20 psi pressure was obtained (repeated two times). After refilling the reactor with hydrogen the mixture was hydrogenolized at 20 psi and 30±5° C. for 2 hours. The palladium carbon was removed using Hyflow bed on Nutsche filter, washed with i-PrOH (18.0 L), and the combined filtrates were concentrated under high vacuum (NLT650 mm/Hg) till absence of distillate at below 50° C. The fesh i-PrOH (9.0 L) was added to the residue, and the mixture was concentrated under high vacuum (NLT650 mm/Hg) till absence of distillate at below 50° C.

The concentrated material was dissolved in IPA (45.0 L), transferred to the clean reactor, cooled to 7.5±2.5° C. and treated with thiosilica (0.18 kg) and stirred for 3 hours at 7.5±2.5° C. The thiosilica was removed by filtration through Hyflow bed on Nutsche filter, washed with i-PrOH (18.0 L), and the combined filtrates were concentrated under high vacuum (NLT650 mm/Hg) till absence of distillate at below 50° C.

Heptane (13.5 L) was added to the above mixture and concentrated under high vacuum (NLT650 mm/Hg) till absence of distillate at below 50° C. Further heptane (13.5 L) was added to the above mixture and concentrated under high vacuum (NLT650 mm/Hg) till absence of distillate at below 50° C. Heptane (22.5 L) was added to the above mixture and the resulting suspension was stirred for 90 minutes at 20±5° C. The product was isolated by centrifuge filtration, and washed with heptane (9.0 L). The wet cake was dried at 30±5° C. under high vacuum (NLT 650 mm/Hg) for 10 hours to afford crude title product (2.9 kg).

Recrystallisation

A solution of crude 3'-N-Demethyl-4"-O-(2-diethylaminoethanoyl)-6-O-methyl-9a-aza-9a-homoerythromycin A (4.2 kg) in isopropyl acetate (33.6 L) at 27.5±2.5° C. was stirred for 10 minutes, then additional amount of isopropyl acetate (12.6 L) was added till clear solution was observed. The solution was filtered through Micron filter, washed with isopropyl acetate (2.1 L) transferred to the clear reactor and seeded with 3'-N-Demethyl-4"-O-(2-diethylaminoethanoyl)-6-O-methyl-9a-aza-9a-homoerythromycin A, Form 1 (0.01 kg). The resulting mixture was stirred for 30 minutes at 27.5±2.5° C., then heptane (96.6 L) was added slowly 2 hours at 27.5±2.5° C. The suspension was stirred for 12 hours 10 minutes at 27.5±2.5° C., cooled to 2.5±2.5° C. and stirred for 2.5 hours at this temperature. The product was isolated by filtration, washed with chilled heptane:isopropyl acetate mixture (2:15.65 L/2.74 L) and finally heptane (8.4 L). The product was dried at 40±5° C. under high vacuum (NLT 650 mm/Hg) to constant weight to afford 3'-N-Demethyl-4"-O-(2-diethylaminoethanoyl)-6-O-methyl-9a-aza-9a-homoerythromycin A, Form 1 (3.46 kg), $^1$H NMR profile conforms to reference, HPLC purity 98.0%).

Comparative Example 2

3'-N-Demethyl-4"-O-(3-diethylaminopropionoyl)-6-O-methyl-9a-aza-9a-homoerythromycin A

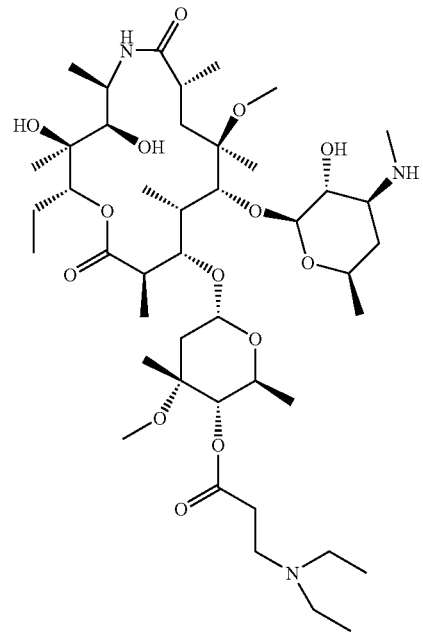

Using the procedure of Example 54 in international publication WO2006/087644, the title compound was obtained.

MS data (MS (ES+) m/z: 876.7 [MH]+) conforms to that stated in WO2006/087644.

Comparative Example 3

4"-O-(2-diethylaminoethanoyl)-6-O-methyl-9a-aza-9a-homoerythromycin A

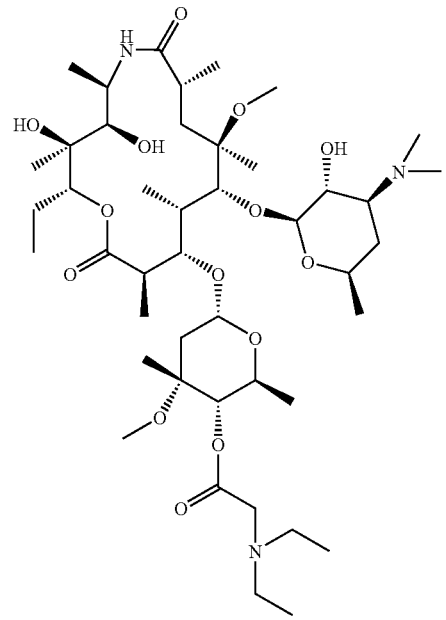

Using the procedure of Example 56 in international publication WO2006/087644, the title compound was obtained.

MS data (MS (ES+) m/z: 877.09 [MH]+) conforms to that stated in WO2006/087644.

Example 4

3'-N-Demethyl-4"-O-(2-diethylaminoethanoyl)-6-O-methyl-9a-aza-9a-homoerythromycin A Acetate Salt 3'-N-Demethyl-4"-O-(2-diethylaminoethanoyl)-6-O-methyl-9a-aza-9a-homoerythromycin A (100 mg, 0.116 mmol) was dissolved in i-PrOH (0.7 mL) and acetic acid (13.9 µL, 0.244 mmol) was added. Mixture was cooled at 0° C. and n-hexane (10 mL) and diisopropyl-ether (3 mL) were added dropwise. Then, solvents were evaporated, yielding after drying title compound (103 mg) as white solid.

MS (ES+) m/z: 862.8 (95.3%)

Example 5

3'-N-Demethyl-4"-O-(2-diethylaminoethanoyl)-6-O-methyl-9a-aza-9a-homoerythromycin A Succinate Salt 3'-N-Demethyl-4"-O-(2-diethylaminoethanoyl)-6-O-methyl-9a-aza-9a-homoerythromycin A (75 mg), succinic acid (20 mg) and t-butylacetate (300 µL) were added into a vial and temperature cycled from 0 to 40° C. over 2 days under stirring. The slurry was isolated and the obtained solid dried at 40° C. under vacuum for 60 hours to afford the title product.

$^1$H NMR (400 MHz, CHLOROFORM-d) δ ppm 7.61, 6.46, 6.44, 6.12, 6.10, 5.21, 5.08, 5.06, 4.93, 4.92, 4.89, 4.88, 4.75, 4.72, 4.69, 4.67, 4.60, 4.58, 4.54, 4.53, 4.51, 4.49, 4.37, 4.36, 4.34, 4.33, 4.32, 4.21, 4.19, 4.17, 4.15, 4.08, 4.06, 3.82, 3.77, 3.74, 3.72, 3.65, 3.64, 3.61, 3.55, 3.51, 3.48, 3.44, 3.31, 3.31, 3.28, 3.22, 3.06, 3.05, 3.03, 3.01, 2.85, 2.84, 2.82, 2.73, 2.71, 2.69, 2.67, 2.58, 2.56, 2.54, 2.52, 2.41, 2.37, 2.31, 2.24, 2.22, 2.10, 2.07, 2.04, 1.99, 1.97, 1.92, 1.90, 1.88, 1.86, 1.79, 1.66, 1.64, 1.61, 1.59, 1.57, 1.56, 1.52, 1.51, 1.50, 1.48, 1.47, 1.45, 1.43, 1.42, 1.40, 1.32, 1.29, 1.28, 1.26, 1.23, 1.22, 1.18, 1.17, 1.16, 1.14, 1.13, 1.12, 1.10, 1.08, 1.06, 0.99, 0.97, 0.92, 0.90, 0.88.

Example 6

3'-N-Demethyl-4"-O-(2-diethylaminoethanoyl)-6-O-methyl-9a-aza-9a-homoerythromycin A Benzoic Salt 3'-N-Demethyl-4"-O-(2-diethylaminoethanoyl)-6-O-methyl-9a-aza-9a-homoerythromycin A (75 mg), benzoic acid (10.6 mg) and t-butylacetate (300 µL) were added into a vial and temperature cycled from 0 to 40° C. over 2 days under stirring. The slurry was isolated and the obtained solid dried at 40° C. under vacuum for 60 hours to afford the title product.

$^1$H NMR (400 MHz, CHLOROFORM-d) δ ppm 8.08, 8.06, 7.52, 7.51, 7.49, 7.44, 7.42, 7.40, 7.27, 6.11, 6.09, 4.89, 4.88, 4.74, 4.71, 4.70, 4.67, 4.60, 4.58, 4.39, 4.38, 4.37, 4.35, 4.34, 4.21, 4.20, 4.18, 4.16, 3.75, 3.74, 3.49, 3.44, 3.40, 3.38, 3.36, 3.35, 3.32, 3.31. 3.22, 2.85, 2.83, 2.82, 2.80, 2.74, 2.72, 2.70, 2.68, 2.59, 2.40, 2.37, 2.24, 2.22, 2.20, 2.05, 2.05, 2.02, 2.01, 1.99, 1.97, 1.88, 1.86, 1.65, 1.64, 1.61, 1.60, 1.57, 1.55, 1.45, 1.41, 1.38, 1.33, 1.30, 1.25, 1.23, 1.22, 1.20, 1.19, 1.17, 1.15, 1.13, 1.11, 1.10, 1.08, 1.06, 0.99, 0.97, 0.92, 0.90, 0.89.

Example 7

3'-N-Demethyl-4"-O-(2-diethylaminoethanoyl)-6-O-methyl-9a-aza-9a-homoerythromycin A L-tartrate Salt 3'-N-Demethyl-4"-O-(2-diethylaminoethanoyl)-6-O-methyl-9a-aza-9a-homoerythromycin A (75 mg), L-tartaric acid (13.5 mg) and t-butylacetate (300 µL) were added into a vial and temperature cycled from 0 to 40° C. over 2 days under stirring. The slurry was isolated and the obtained solid dried at 40° C. under vacuum for 60 hours to afford the title product.

$^1$H NMR (400 MHz, CHLOROFORM-d) δ ppm 7.19, 7.17, 7.10, 7.08, 6.14, 6.12, 4.81, 4.80, 4.66, 4.63, 4.61, 4.59, 4.49, 4.48, 4.32, 4.30, 4.29, 4.28, 4.23, 4.12, 4.11, 4.09, 4.07, 3.72, 3.71, 3.70, 3.67, 3.66, 3.42, 3.38, 3.27, 3.24, 3.12, 2.78, 2.76, 2.75, 2.67, 2.65, 2.63, 2.61, 2.51, 2.32, 2.28, 2.17, 2.15, 2.13, 1.95, 1.93, 1.90, 1.89, 1.82, 1.81, 1.79, 1.61, 1.57, 1.56, 1.53, 1.52, 1.37, 1.25, 1.22, 1.18, 1.16, 1.14, 1.12, 1.10, 1.09, 1.07, 1.05, 1.03, 1.01, 0.99, 0.94, 0.92, 0.85, 0.83, 0.81.

Example 8

3'-N-Demethyl-4"-O-(2-diethylaminoethanoyl)-6-O-methyl-9a-aza-9a-homoerythromycin A di-hydrochloride Salt 3'-N-Demethyl-4"-O-(2-diethylaminoethanoyl)-6-O-methyl-9a-aza-9a-homoerythromycin A (100 mg) and acetonitrile (200 µL) were added into a vial. Slurry obtained was stirred and heated to 70° C. An additional amount of acetonitrile (300 µL) was added followed by addition of hydrochloric acid (19 µL, 37% w/w in water) which resulted in formation of solid and difficult stirring. Thus, a further amount of acetonitrile (200 µL) was added and the reaction mixture cooled to 0° C. and maintained at that temperature for 15 hours. The slurry was filtered and the obtained solid dried at 40° C. under vacuum for 24 hours to afford the title product.

$^1$H NMR (400 MHz, CHLOROFORM-d) δ ppm 7.57, 7.55, 5.10, 5.09, 4.99, 4.98, 4.96, 4.96, 4.93, 4.87, 4.85, 4.83, 4.53, 4.52, 4.49, 4.48, 4.46, 4.45, 4.44, 4.42, 4.14, 4.12, 4.11, 3.82, 381, 3.71, 3.69, 3.63, 3.48, 3.48, 3.47, 3.38, 3.36, 3.34, 3.32, 3.31, 3.31, 3.31, 3.30, 3.30, 3.28, 3.25, 3.21, 3.12, 3.11, 3.09, 3.07, 3.06, 2.81, 2.79, 2.78, 2.77, 2.76, 2.72, 2.69, 2.51, 2.47, 2.40, 2.38, 2.38, 2.36, 2.34, 2.26, 2.23, 2.22, 2.20, 2.03, 2.02, 2.00, 1.99, 1.89, 1.88, 1.87, 1.86, 1.85, 1.85, 1.83, 1.83, 1.78, 1.77, 1.75, 1.73, 1.56, 1.55, 1.54, 1.53, 1.52, 1.51, 1.50, 1.48, 1.43, 1.40, 1.37, 1.35, 1.33, 1.31, 1.29, 1.24, 1.23, 1.22, 1.21, 1.19, 1.18, 1.17, 1.15, 1.14, 1.12, 1.06, 1.04, 1.03, 1.01, 0.92, 0.90, 0.88.

Example 9

3'-N-Demethyl-4"-O-(2-diethylaminoethanoyl)-6-O-methyl-9a-aza-9a-homoerythromycin A Phosphate Salt 3'-N-Demethyl-4"-O-(2-diethylaminoethanoyl)-6-O-methyl-9a-aza-9a-homoerythromycin A (75 mg), phosphoric acid (6 µL, 85% w/w in water) and t-butylacetate (300 µL) were added into a vial and temperature cycled from 0 to 40° C. over 2 days under stirring. The slurry was isolated and the obtained solid dried at 40° C. under vacuum for 60 hours to afford the title product.

¹H NMR (400 MHz, CHLOROFORM-d) δ ppm 7.19, 7.17, 7.10, 7.08, 6.07, 4.81, 4.80, 4.65, 4.62, 4.59, 4.48, 4.46, 4.30, 4.13, 4.11, 4.09, 4.07, 3.65, 3.64, 3.58, 3.54, 3.49, 3.25, 3.23, 3.14, 2.77, 2.75, 2.72, 2.70, 2.51, 2.32, 2.28, 2.16, 2.15, 2.13, 1.96, 1.94, 1.92, 1.89, 1.84, 1.82, 1.80, 1.78, 1.77, 1.61, 1.57, 1.55, 1.53, 1.52, 1.47, 1.45, 1.38, 1.35, 1.25, 1.19, 1.17, 1.16, 1.13, 1.12, 1.10, 1.09, 1.07, 1.05, 1.04, 1.03, 1.02, 1.02, 0.92, 0.90, 0.84, 0.83, 0.81.

Example 10

3'-N-Demethyl-4"-O-(2-diethylaminoethanoyl)-6-O-methyl-9a-aza-9a-homoerythromycin A Amorphous Form 3'-N-Demethyl-4"-O-(2-diethylaminoethanoyl)-6-O-methyl-9a-aza-9a-homoerythromycin A (1.33 g) obtained according to the similar procedure of the above Example 1, Method A, Method 1, was dissolved in acetone and then precipitated by addition of petrolether to afford the title product (1.2 g) as amorphous form characterized by XRPD pattern FIG. 3.

MS (ES+) m/z: 862.47 [MH]+.

Example 11

3'-N-Demethyl-4"-O-(2-diethylaminoethanoyl)-6-O-methyl-9a-aza-9a-homoerythromycin A—Form 1

Amorphous 3'-N-Demethyl-4"-O-(2-diethylaminoethanoyl)-6-O-methyl-9a-aza-9a-homoerythromycin A, Example 10 (500 mg) was dissolved in acetonitrile (2.5 mL) at room temperature by stirring. Within 1-2 minutes after a clear solution was obtained, a substance started to precipitate. The suspension was stirred for 1.5 hours at room temperature. The white precipitate was filtered under vacuum, washed with acetonitrile (3×0.5 mL) and dried at room temperature for 1 hour to afford the title product (307 mg) Form 1. Isolated solid material was analysed by XRPD, DSC and TGA.

The acquisition conditions for XRPD were as specified under a). The XRPD pattern of Form 1 is provided in FIG. 4. The DSC of Form 1 provided in FIG. 5 shows broad endotherm with onset at 148.97° C. and peak at 156.21° C. The TGA of Form 1 provided in FIG. 6 shows weight loss of 0.29%.

Example 12

3'-N-Demethyl-4"-O-(2-diethylaminoethanoyl)-6-O-methyl-9a-aza-9a-homoerythromycin A—Form 2

Amorphous 3'-N-Demethyl-4"-O-(2-diethylaminoethanoyl)-6-O-methyl-9a-aza-9a-homoerythromycin A, Example 10 (100 mg) was added to demineralised water (1.0 mL). To the obtained suspension acetone (1 mL) was added resulting in gum like material. An additional amount of acetone (0.4 mL) was added and the gum like material dissolved by slightly heating. Further demineralised water (0.4 mL) was added. About 90% of the clear solution was transferred to a new vial which was then covered by parafilm, and maintained at room temperature to crystallize. After 15 days obtained crystals (single crystals, small hexagons) were isolated by filtration to afford title product (23 mg) Form 2.

Isolated crystals were maintained at air and ambient temperature for two hours, and analysed by XRPD, DSC and TGA.

The acquisition conditions for XRPD were as specified under a). The XRPD pattern of Form 2 is provided in FIG. 7.

The DSC of Form 2 provided in FIG. 8 shows broad endotherm with onset at 144.79° C. and peak at 151.65° C. The TGA of Form 2 is provided in FIG. 9.

Example 13

3'-N-Demethyl-4"-O-(2-diethylaminoethanoyl)-6-O-methyl-9a-aza-9a-homoerythromycin A—Form 3

3'-N-Demethyl-4"-O-(2-diethylaminoethanoyl)-6-O-methyl-9a-aza-9a-homoerythromycin A, Form 1 (700 mg) was placed into a Syn$^{10}$ tube with methanol:water 50% (3 mL). The slurry was temperature cycled from 0 to 40° C. over 4 days under stirring. The solid was filtered off and dried under vacuum at 40° C. overnight to afford the title product Form 3. Isolated solid material was analysed by ¹H NMR, XRPD and Raman.

¹H NMR (400 MHz, DMSO-D6) showed no presence of solvent peaks.

¹H NMR (400 MHz, DMSO-D6) δ ppm 0.81 (t, J=7.3 Hz, 3H), 0.89 (d, J=6.8 Hz, 4H), 0.92-0.99 (m, 9H), 1.00-1.05 (m, 9H), 1.06-1.13 (m, 9H), 1.22 (s, 3H), 1.38 (s, 1H), 1.66-1.75 (m, 1H), 1.75-1.87 (m, 2H), 1.91 (s, 1H), 2.13 (d, J=13.9 Hz, 1H), 2.25 (s, 3H), 2.31 (d, J=15.4 Hz, 2H), 2.53-2.62 (m, 4H), 2.80-2.87 (m, 1H), 3.13 (s, 2H), 3.14-3.20 (m, 1H), 3.24 (s, 3H), 3.27 (s, 4H), 3.36-3.44 (m, 1H), 3.54 (d, J=6.6 Hz, 1H), 3.70 (s, 1H), 3.85 (s, 1H), 3.94 (d, J=7.3 Hz, 1H), 4.30-4.39 (m, 3H), 4.56 (d, J=9.8 Hz, 1H), 4.77 (d, J=4.6 Hz, 1H), 4.89 (dd, J=9.8, 2.0 Hz, 1H), 5.00 (d, J=4.9 Hz, 1H), 7.17 (d, J=8.3 Hz, 1H).

The acquisition conditions for XRPD were as specified under b). The XRPD pattern of Form 3 is provided in FIG. 10. The Raman spectrum of Form 3 is provided in FIG. 11.

Example 14

3'-N-Demethyl-4"-O-(2-diethylaminoethanoyl)-6-O-methyl-9a-aza-9a-homoerythromycin A—Form 4

3'-N-Demethyl-4"-O-(2-diethylaminoethanoyl)-6-O-methyl-9a-aza-9a-homoerythromycin A, Form 1 (100 mg) and IPA:water=1:1 v:v (0.5 mL) were added into a vial and temperature cycled from 0 to 40° C. over 5 days under stirring. The solution obtained was evaporated at room temperature to afford the title product Form 4. Isolated material was analysed by ¹H NMR and Raman.

¹H NMR (400 MHz, DMSO-D6) δ ppm 7.27, 6.09, 4.89, 4.88, 4.74, 4.71, 4.69, 4.67, 4.58, 4.56, 4.40, 4.23, 4.21, 4.07, 4.05, 4.04, 4.02, 4.00, 3.82, 3.81, 3.80, 3.78, 3.77, 3.75, 3.46, 3.42, 3.34, 3.32, 3.30, 3.25, 3.23, 3.20, 3.17, 3.15, 2.87, 2.86, 2.84, 2.82, 2.80, 2.72, 2.71, 2.69, 2.67, 2.65, 2.62, 2.60, 2.59, 2.46, 2.40, 2.36, 2.26, 2.24, 2.22, 2.20, 2.19, 2.05, 2.03, 2.01, 1.99, 1.95, 1.92, 1.90, 1.88, 1.86, 1.84, 1.65, 1.60, 1.34, 1.32, 1.26, 1.24, 1.23, 1.21, 1.19, 1.17, 1.16, 1.13, 1.12, 1.10, 1.08, 1.06, 1.00, 0.98, 0.92, 0.90, 0.89, 0.01. Raman spectrum of Form 4 is provided in FIG. 12.

Example 15

3'-N-Demethyl-4"-O-(2-diethylaminoethanoyl)-6-O-methyl-9a-aza-9a-homoerythromycin A—Form 5

Method A: 3'-N-Demethyl-4"-O-(2-diethylaminoethanoyl)-6-O-methyl-9a-aza-9a-homoerythromycin A, Form 1 (25 mg) was slurried in isopropyl ether (500 μL) and temperature cycled from 0 to 40° C. for 24 hours under shaking. Then, with the temperature set at 20° C., the reaction mixture was shaken for 2 days. The solid was filtered off and dried under vacuum for 1 hour to afford the title product Form 5. Isolated solid material was analysed by Raman. Raman spectrum of Form 5 is provided in FIG. 13.

Method B: 3'-N-Demethyl-4"-O-(2-diethylaminoethanoyl)-6-O-methyl-9a-aza-9a-homoerythromycin A, Form 1 (25 mg) was slurried in t-butyl methyl ether (500 μL) and temperature cycled from 0 to 40° C. for 24 hours under shaking. Then, with the temperature set at 20° C., an additional amount of 3'-N-Demethyl-4"-O-(2-diethylaminoethanoyl)-6-O-methyl-9a-aza-9a-homoerythromycin A, Form 1 (cca 25 mg) was added spatula-wise to obtain a thick slurry which was shaken for 2 days at 20° C. The solid was filtered off and dried under vacuum for 1 hour to afford the title product Form 5, which was according to Raman spectrum concondant with the material obtained in Example 15, Method A. $^1$H NMR (400 MHz, DMSO-D6) showed no presence of solvent peaks.

$^1$H NMR (400 MHz, DMSO-D6) δ ppm 0.81 (t, J=7.5 Hz, 3H), 0.89 (d, J=6.8 Hz, 4H), 0.92-0.99 (m, 9H), 1.00-1.05 (m, 9H), 1.06-1.14 (m, 9H), 1.22 (s, 3H), 1.31-1.46 (m, 1H), 1.63-1.73 (m, 1H), 1.75-1.86 (m, 2H), 1.87-1.97 (m, 1H), 2.11 (s, 1H), 2.25 (s, 3H), 2.31 (d, J=15.4 Hz, 2H), 2.59 (qd, J=7.2, 1.6 Hz, 4H), 2.84 (d, J=6.1 Hz, 1H), 3.13 (s, 2H), 3.15-3.19 (m, 1H), 3.24 (s, 3H), 3.25-3.28 (m, 4H), 3.35-3.45 (m, 1H), 3.54 (d, J=6.6 Hz, 1H), 3.70 (s, 1H), 3.85 (s, 1H), 3.96 (d, J=7.8 Hz, 1H), 4.30-4.40 (m, 3H), 4.56 (d, J=10.0 Hz, 1H), 4.77 (d, J=4.6 Hz, 1H), 4.89 (dd, J=9.9, 2.1 Hz, 1H), 5.00 (d, J=4.6 Hz, 1H), 7.17 (d, J=8.1 Hz, 1H).

Example 16

3'-N-Demethyl-4"-O-(2-diethylaminoethanoyl)-6-O-methyl-9a-aza-9a-homoerythromycin A—Form 6

A solution of 3'-N-Demethyl-4"-O-(2-diethylaminoethanoyl)-6-O-methyl-9a-aza-9a-homoerythromycin A, Form 1 (50 mg) in methyl acetate (500 μL) was temperature cycled from 0 to 40° C. for 24 hours under shaking. Then, with the temperature set at 20° C., an additional amount of 3'-N-Demethyl-4"-O-(2-diethylaminoethanoyl)-6-O-methyl-9a-aza-9a-homoerythromycin A, Form 1 (cca 50 mg) was added spatula-wise to obtain a thick slurry which was shaken for 2 days at 20° C. The slurry was filtered off and 300 μL of the saturated filtrate was capped and placed in the fridge at cca 2° C. for 1 month to afford the title product Form 6, which was isolated by careful pipetting of the solution. The solid was dried briefly under nitrogen flow before analysis by Raman. $^1$H NMR (in DMSO-d6) did not show a presence of solvent. Baseline corrected Raman spectrum of Form 6 is provided in FIG. 14.

Example 17

3'-N-Demethyl-4"-O-(2-diethylaminoethanoyl)-6-O-methyl-9a-aza-9a-homoerythromycin A—Form 7

3'-N-Demethyl-4"-O-(2-diethylaminoethanoyl)-6-O-methyl-9a-aza-9a-homoerythromycin A, Form 1 (75 mg) was placed in HPLC vial insert, placed into HPLC vial containing tetrahydrofuran (1.5 mL), cap tightened and left at ambient temperature for 5 days causing the solid to deliquesce. The 1/3 of the resulting solution was placed in a new HPLC vial insert which was placed into a HPLC vial containing n-pentane (1.5 mL) and left at the ambient temperature over two weeks to afford the title product Form 7, which was isolated by careful pipetting of the solution. The solid was dried briefly under nitrogen flow before analysis by Raman. $^1$H NMR (in DMSO-d6) showed a presence of THF (<0.25 eq). Raman spectrum of Form 7 is provided in FIG. 15.

Example 18

3'-N-Demethyl-4"-O-(2-diethylaminoethanoyl)-6-O-methyl-9a-aza-9a-homoerythromycin A—Form 8

A solution of 3'-N-Demethyl-4"-O-(2-diethylaminoethanoyl)-6-O-methyl-9a-aza-9a-homoerythromycin A, Form 1 (200 mg) in methanol (500 μL) was temperature cycled from 0 to 40° C. for 24 hours under shaking. Then, with the temperature set at 20° C., an additional amount of 3'-N-Demethyl-4"-O-(2-diethylaminoethanoyl)-6-O-methyl-9a-aza-9a-homoerythromycin A, Form 1 (cca 175 mg) was added spatula-wise to obtain a thick slurry which was shaken for 2 days at 20° C. The slurry was filtered off and 200 μL of the filtrate was diluted by methanol (200 μL). An aliquot of 200 μL was placed in the evaporation plate and allowed to evaporate to dryness to afford the title product Form 6. Isolated material was analysed by Raman. Raman spectrum of Form 8 is provided in FIG. 16.

Results
Stability

In Vitro Blood and Plasma Stability

Figure 1B:
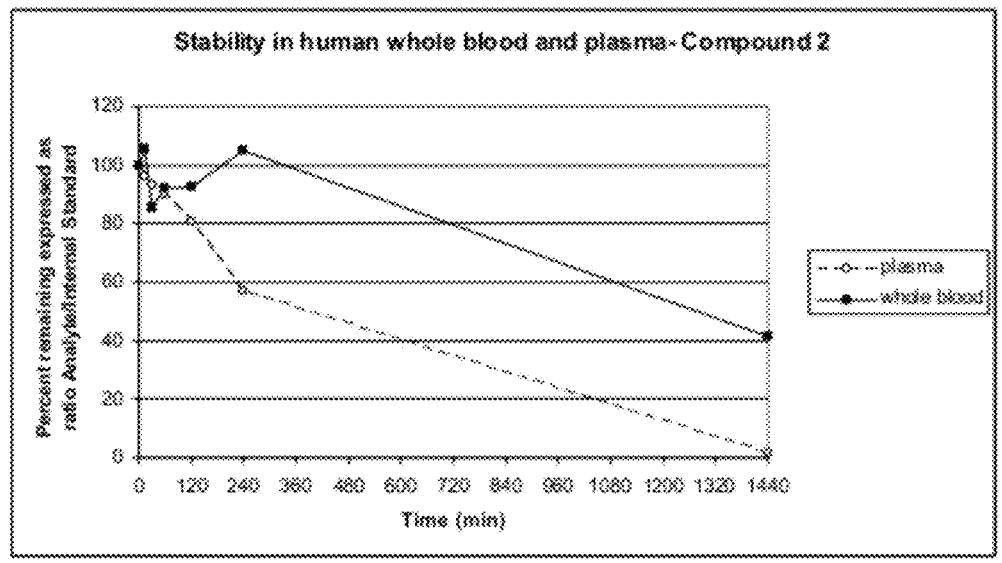
Figure 1C:
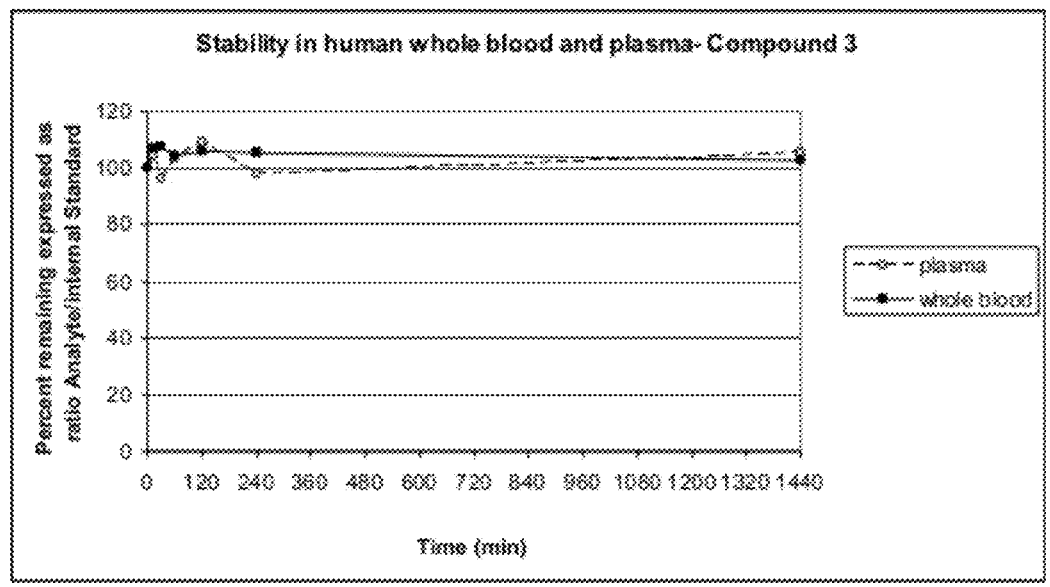
Figure 1C:
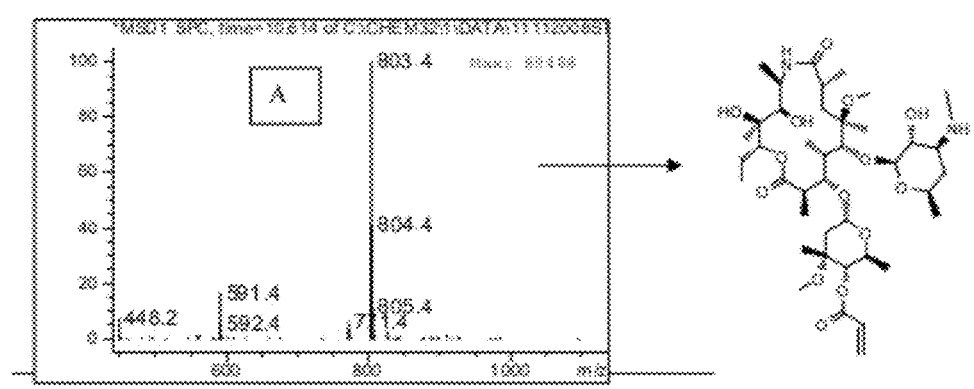

The in vitro stability of the compounds of examples 1 to 3 was measured using the methodology described in In vitro blood and plasma stability protocol. Examples 1 and 3 showed to be stable both in whole blood and in plasma over 24 hours. After 24 hours, Example 2 showed instability, with around 41% compound remaining in whole blood and less than 2% in plasma (see FIGS. 1A-C).

Stability in Buffer Solutions and in Bio-Relevant Media

The stability of the compounds of examples 1 to 3 was measured in buffer solutions pH2 to pH8 at 25° C. and in bio-relevant media (SGF pH 1.6, Fasted SIF pH 6.5 and Fed SIF pH 5.0) at 37° C., during 24 hours using the methodology described in *Stability in buffer solutions and in bio-relevant media protocol*.

The results of solution stability testing in different buffers are shown in Table 1, and of solution stability testing in physiologically relevant media are shown in Table 2.

TABLE 1

Percentage (Area %) of the compound observed in buffers pH 2 to pH 8 during 24 hours at 25° C.
Stability in buffers pH 2 to pH 8 at 25° C.

| Ex | Initial | 2 h | 4 h | 6 h | 8 h | 12 h | 14 h | 18 h | 20 h | 22 h | 24 h |
|---|---|---|---|---|---|---|---|---|---|---|---|
| pH 2 | | | | | | | | | | | |
| 1 | 100 | 97.5 | 96.9 | 96.6 | 96.1 | 96.1 | NA | NA | NA | NA | 95.9 |
| 2 | 100 | 100 | 100 | 98.7 | 98.5 | 97.6 | 97.6 | 97.5 | 97.3 | 97.2 | 97.2 |
| 3 | 100 | 99.4 | 99.5 | 99.5 | 99.5 | 99.6 | 99.6 | 99.6 | 99.5 | 99.5 | 99.5 |
| pH 3 | | | | | | | | | | | |
| 1 | 100 | 100 | 99.9 | 99.9 | 99.6 | 99.4 | NA | NA | NA | NA | 99.4 |
| 2 | 100 | 100 | 100 | 98.8 | 97.5 | 97.3 | 97.3 | 97.0 | 97.0 | 97.0 | 96.9 |
| 3 | 100 | 99.8 | 99.6 | 99.5 | 99.8 | 99.6 | 99.8 | 99.7 | 99.6 | 99.4 | 99.4 |
| pH 4 | | | | | | | | | | | |
| 1 | 100 | 100 | 99.9 | 100 | 99.8 | 99.6 | NA | NA | NA | NA | 99.5 |
| 2 | 100 | 100 | 100 | 100 | 99.3 | 99.0 | 98.5 | 98.5 | 98.4 | 98.4 | 98.3 |
| 3 | 100 | 99.1 | 99.0 | 99.1 | 99.2 | 99.2 | 99.2 | 99.2 | 98.9 | 99.1 | 99.2 |
| pH 5 | | | | | | | | | | | |
| 1 | 100 | 100 | 100 | 100 | 99.8 | 99.6 | NA | NA | NA | NA | 99.1 |
| 2 | 100 | 98.5 | 98.5 | 98.4 | 98.4 | 98.4 | 98.3 | 98.3 | 98.3 | 98.3 | 98.0 |
| 3 | 100 | 100 | 99.9 | 99.9 | 99.9 | 99.9 | 99.9 | 99.9 | 99.8 | 99.9 | 99.9 |
| pH 6 | | | | | | | | | | | |
| 1 | 100 | 100 | 99.5 | 99.5 | 98.7 | 98.7 | NA | NA | NA | NA | 98.7 |
| 2 | 100 | 99.6 | 99.4 | 99.0 | 99.0 | 99.0 | 98.5 | 98.3 | 98.2 | 98.2 | 98.1 |
| 3 | 100 | 100 | 100 | 100 | 100 | 99.9 | 99.8 | NA | 99.7 | 99.7 | 99.7 |
| pH 7 | | | | | | | | | | | |
| 1 | 100 | 100 | 100 | 99.9 | 99.8 | 99.8 | NA | NA | NA | NA | 99.1 |
| 2 | 100 | 97.8 | 93.4 | 89.8 | 89.3 | 85.1 | 84.3 | 84.0 | 81.3 | 79.9 | 78.4 |
| 3 | 100 | 100 | 99.9 | 99.9 | 99.9 | 99.7 | 99.7 | 99.8 | 98.8 | 99.7 | 98.7 |
| pH 8 | | | | | | | | | | | |
| 1 | 100 | 100 | 100 | 99.9 | 99.5 | 99 | NA | NA | NA | NA | 97.1 |
| 2 | 100 | 92.0 | 81.7 | 77.7 | 71.7 | 63.4 | 60.2 | 54.2 | 51.1 | 47.1 | 44.6 |
| 3 | 100 | 99.9 | 99.9 | 99.9 | 99.7 | 99.5 | 99.4 | 98.4 | 98.3 | 98.2 | 98.2 |

NA = not analysed

Examples 1 and 3 showed stability in buffers pH 2 to 8.

Example 2 showed instability in buffers at pH 7 and at pH 8.

After 24 hours at 25° C. in buffer solution pH 7 there was 78.4% of Example 2 remaining. After 24 hours at 25° C. in buffer solution pH 8 there was 44.6% of Example 2 remaining.

According to MS data, the major degradant of Example 2 at pH 7 and pH 8 is 3'-N-demethyl-4"-O-acryloyl-6-O-methyl-9a-aza-9a-homoerythromycin A (see FIG. 2).

TABLE 2

Percentage (Area %) of the compound observed in Bio-relevant media during 24 hours at 37° C.

Stability in Bio-relevant media at 37° C.

| Ex | Initial | 1 h | 1.5 h | 2 h | 3 h | 4 h | 4.3 h | 5 h | 6 h | 8 h | 10 h | 12 h | 15 | 18 h | 20 h | 21 h | 24 h |
|---|---|---|---|---|---|---|---|---|---|---|---|---|---|---|---|---|---|
| SGF pH 1.6 | | | | | | | | | | | | | | | | | |
| 1 | 100 | NA | 99.7 | 98.8 | 98.7 | NA | 95.6 | NA | NA | NA | NA | NA | NA | NA | 95.4 | NA | 95.0 |
| 2 | 100 | 99.3 | NA | 99.3 | 96.6 | 92.9 | NA | 92.3 | 91.1 | 90.1 | 87.2 | 85.4 | 83.9 | 82.4 | NA | 81.0 | 79.0 |
| 3 | 100 | 98.5 | NA | 98.5 | 98.0 | 98.0 | NA | 98.0 | 95.9 | 95.7 | 95.0 | 95.0 | NA | NA | NA | NA | 94.5 |

TABLE 2-continued

Percentage (Area %) of the compound observed in Bio-relevant media during 24 hours at 37° C.

Stability in Bio-relevant media at 37° C.

| Ex | Initial | 1 h | 1.5 h | 2 h | 3 h | 4 h | 4.3 h | 5 h | 6 h | 8 h | 10 h | 12 h | 15 | 18 h | 20 h | 21 h | 24 h |
|---|---|---|---|---|---|---|---|---|---|---|---|---|---|---|---|---|---|
| | | | | | | Fasted SIF pH 6.5 | | | | | | | | | | | |
| 1 | 100 | NA | 99.7 | 99.6 | 99.2 | NA | 98.8 | NA | NA | NA | NA | NA | NA | NA | 95.4 | NA | 94.7 |
| 2 | 100 | 99.6 | NA | 98.0 | 93.0 | 89.7 | NA | 86.7 | NA | NA | NA | NA | NA | NA | NA | NA | 63.7 |
| 3 | 100 | 99.2 | NA | 98.7 | 98.3 | 97.8 | NA | 97.6 | NA | NA | NA | NA | NA | NA | NA | NA | 95.1 |
| | | | | | | Fed SIF pH 5.0 | | | | | | | | | | | |
| 1 | 100 | 99.9 | NA | 99.8 | NA | NA | 98.3 | NA | NA | NA | NA | NA | NA | NA | NA | NA | 99.1 |
| 2 | 100 | 99.7 | NA | 99.6 | 99.4 | 98.7 | NA | 98.6 | NA | NA | NA | NA | NA | NA | NA | NA | 97.4 |
| 3 | 100 | 100 | NA | 99.9 | 100 | 99.9 | NA | 99.8 | NA | NA | NA | NA | NA | NA | NA | NA | 99.8 |

NA = not analysed

Examples 1 and 3 showed stability in all three bio relevant media.
Example 2 showed instability in bio-relevant media SGF pH 1.6 and in Fasted SIF pH 6.5.
After 24 hours at 37° C. in SGF pH 1.6 there was 79.0% of Example 2 remaining.
After 24 hours at 37° C. in Fasted SIF pH 6.5 there was 63.7% of Example 2 remaining.

In Vitro Assay

The in vitro potency of the compounds of examples 1 to 3 as an anti-bacterial agent has been measured using the methodology described in the in vitro protocol. Examples 1 and 2 were found to have no measurable activity against all six strains (MIC>64 μg/mL in each case). Example 3 was found to show anti-bacterial activity, with a minimal inhibitory concentration (MIC) of 8 μg/mL against *Moraxella catarrhalis* ATCC23246 and against *Streptococcus pneumoniae* ATCC49619, whereas against the other four strains it showed no measurable activity (MIC>64 μg/mL in each case).

In Vivo Assay

The in vivo potency of the compounds of examples 1 to 3 as an anti-inflammatory agent has been measured using the methodology described in the in vivo protocol for Lung neutrophilia induced by bacterial lipopolysaccharide in male BALB/cJ mice (as here and before described) and/or in the in vivo protocol Lung neutrophilia induced by bacterial lipopolysaccharide in male BALB/cJ mice as described in international publication WO2006/087644. Examples 1, 2 and 3 showed an average of more than 90% inhibition of total cell number. On average Example 1 showed more than 89%, example 2 showed more than 70%, and example 3 showed more than 79% of inhibition of the number of neutrophils in BALF of treated animals which received intraperitoneally (i.p.) a single dose of 200 mg/kg of test compound.

Overall Profile

The compound of Example 1 has an advantageous profile in that it shows potency in an anti-inflammatory screen, does not have significant anti-bacterial activity, and is stable in plasma, whole blood, in buffer solutions from pH 2 to pH 8 and in bio-relevant media, rendering it highly suitable for development as an anti-inflammatory agent.

What is claimed is:

1. The compound 3'-N-demethyl-4"-O-(2-diethylaminoethanoyl)-6-O-methyl-9a-aza-9a-homoerythromycin A, having the Formula (I):

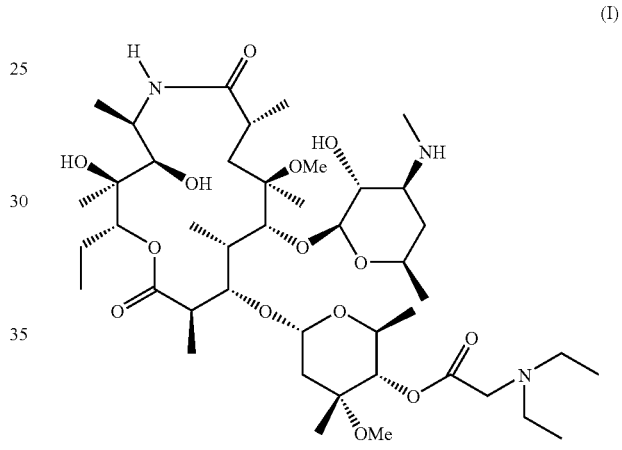

or a salt thereof.

2. The compound of Formula (I) as claimed in claim 1 or a pharmaceutically acceptable salt thereof.

3. A compound as claimed in claim 1, which is 3'-N-demethyl-4"-O-(2-diethylaminoethanoyl)-6-O-methyl-9a-aza-9a-homoerythromycin A, having the Formula (I):

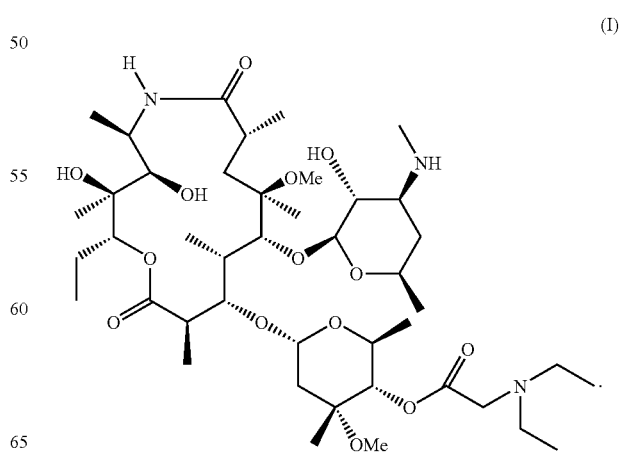

4. A compound of Formula (I) as claimed in claim 1, which is a crystalline form of 3'-N-demethyl-4"-O-(2-diethylamino-ethanoyl)-6-O-methyl-9a-aza-9a-homoerythromycin A.

5. A crystalline form of Formula (I) as claimed in claim 4, which is Form 1 characterized by the XRPD pattern expressed in terms of 2 theta angles and obtained with a diffractometer using copper Kα radiation, wherein the XRPD pattern comprises 2 theta angles (2Θ/°) in at least five positions selected from the group consisting of: 4.6, 5.6, 7.7, 9.6, 10.6, 11.0, 11.6, 11.8, 12.2, 14.1, 15.9, 18.4, 19.0, 20.5, 21.1 and 22.0 degrees, which correspond respectively to d-spacings at 19.1, 15.9, 11.5, 9.2, 8.4, 8.0, 7.7, 7.5, 7.2, 6.3, 5.6, 4.8, 4.7, 4.3, 4.2 and 4.0 Angstroms (Å).

6. A crystalline form of Formula (I) as claimed in claim 4, which is Form 2 characterized by the XRPD pattern expressed in terms of 2 theta angles and obtained with a diffractometer using copper Kα radiation, wherein the XRPD pattern comprises 2 theta angles (2Θ/°) in at least five positions selected from the group consisting of: 9.1, 9.4, 10.4, 10.9, 11.5, 12.0, 13.0, 13.4, 14.7, 15.4, 15.7, 16.5, 16.8, 18.7, 19.2, 19.5, 19.8 and 20.8, which correspond respectively to d-spacings at 9.7, 9.5, 8.5, 8.1, 7.7, 7.4, 6.8, 6.6, 6.0, 5.8, 5.6, 5.4, 5.3, 4.7, 4.6, 4.6, 4.5 and 4.3 Angstroms (Å).

7. A crystalline form of Formula (I) as claimed in claim 4, which is Form 3 characterized by the XRPD pattern expressed in terms of 2 theta angles and obtained with a diffractometer using copper Kα radiation, wherein the XRPD pattern comprises 2 theta angles (2Θ/°) in at least five positions selected from the group consisting of: 5.5, 7.3, 7.9, 9.1, 9.5, 10.0, 10.5, 11.0, 11.5, 12.0, 12.6, 14.8, 15.5, 15.8, 16.6, 16.9, 18.2, 18.9 and 19.5 degrees, which correspond respectively to d-spacings at 16.0, 12.1, 11.3, 9.7, 9.4, 8.9, 8.4, 8.1, 7.7, 7.4, 7.0, 6.0, 5.7, 5.6, 5.3, 5.2, 4.9, 4.7 and 4.6 Angstroms (Å).

8. Process for the preparation of a compound as claimed in claim 1, comprising:
a) reacting a compound of Formula II, wherein $R^1$ is a hydroxy protecting group and $R^2$ is an amino protecting group,

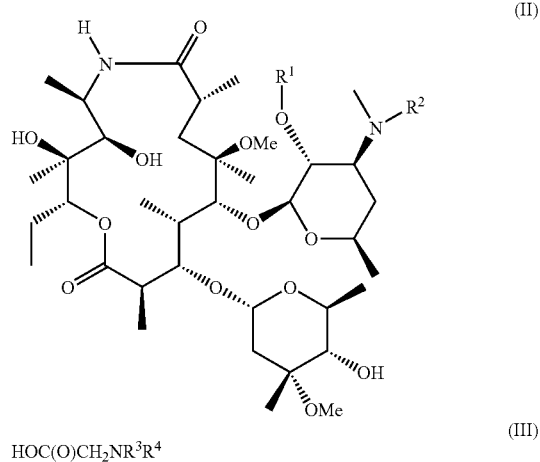

(II)

HOC(O)CH$_2$NR$^3$R$^4$ (III)

with a carboxylic acid or a suitable activated derivative of carboxylic acid of formula (III), wherein $R^3$ and $R^4$ are each ethyl or are independently a group convertible to ethyl, followed by subsequent removal of the hydroxyl protecting group $R^1$, the amino protecting group $R^2$, and where needed, conversion of the —NR$^3$R$^4$ group to —N(CH$_2$CH$_3$)$_2$; or b) by reaction of a compound of formula (IV) wherein L is a suitable leaving group, $R^1$ is a hydroxy protecting group and $R^2$ is an amino protecting group,

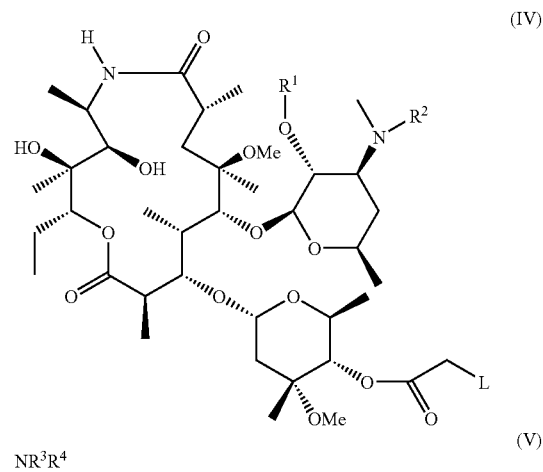

(IV)

NR$^3$R$^4$ (V)

with an amine of formula (V) wherein $R^3$ and $R^4$ are each ethyl or are independently a group convertible to ethyl, followed by subsequent removal of the hydroxyl protecting group $R^1$, the amino protecting group $R^2$, and where needed, conversion of the —NR$^3$R$^4$ group to —N(CH$_2$CH$_3$)$_2$.

9. A method for the treatment of neutrophil dominated inflammatory diseases resulting from neutrophilic infiltration and/or diseases associated with altered cellular functionality of neutrophils selected from chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema, chronic rhinosinusitis, rheumatoid arthritis, gouty arthritis, inflammatory bowel disease, glomerulonephritis, damage from ischemic reperfusion, atherosclerosis, dermatoses such as psoriasis and vasculitis, systemic lupus erythematosus, systemic inflammatory response syndrome, sepsis, ischemia-reperfusion injury, rosacea, periodontitis, gingival hyperplasia and prostatitis syndrome in a subject in need of such treatment comprising administering to the subject a therapeutically effective amount of a compound as claimed in claim 1.

10. The method of claim 9, wherein the disease is selected from chronic obstructive pulmonary disease, cystic fibrosis, diffuse panbronchiolitis, bronchiolitis obliterans, bronchitis, bronchiectasis, acute respiratory distress syndrome, severe or steroid-resistant asthma, emphysema and chronic rhinosinusitis.

11. A pharmaceutical composition comprising a compound as claimed in claim 1, or a pharmaceutically acceptable salt thereof, in association with at least one pharmaceutically acceptable excipient, diluent and/or carrier.

* * * * *